United States Patent
Mansky

(10) Patent No.: US 6,736,017 B2
(45) Date of Patent: May 18, 2004

(54) HIGH THROUGHPUT MECHANICAL RAPID SERIAL PROPERTY TESTING OF MATERIALS LIBRARIES

(75) Inventor: Paul Mansky, San Francisco, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 10/225,793

(22) Filed: Aug. 22, 2002

(65) Prior Publication Data

US 2003/0054740 A1 Mar. 20, 2003

Related U.S. Application Data

(63) Continuation-in-part of application No. 09/939,252, filed on Aug. 24, 2001, and a continuation-in-part of application No. 09/939,139, filed on Aug. 24, 2001.

(51) Int. Cl.[7] .................................................. G01L 3/00
(52) U.S. Cl. ............................... 73/862.046; 73/159
(58) Field of Search ............................. 73/159, 11.01, 73/12.09, 788, 790, 794, 795, 796, 797, 798, 818, 862.046

(56) References Cited

U.S. PATENT DOCUMENTS

| | | |
|---|---|---|
| 1,870,412 A | 8/1932 | Kennedy |
| 3,071,961 A | 1/1963 | Heigl et al. |
| 3,675,475 A | 7/1972 | Weinstein |
| 3,713,328 A | 1/1973 | Aritomi |
| 3,798,960 A | 3/1974 | Glass |
| 3,805,598 A | 4/1974 | Corcoran |
| 3,818,751 A | 6/1974 | Karper et al. |
| 3,849,874 A | 11/1974 | Jeffers |
| 3,895,513 A | 7/1975 | Richardson |
| 3,908,441 A | 9/1975 | Virloget |
| 3,933,032 A | 1/1976 | Tschoegl |
| 4,229,979 A | 10/1980 | Greenwood |
| 4,447,125 A | 5/1984 | Lazay et al. |
| 4,517,830 A | 5/1985 | Gunn et al. |
| 4,567,774 A | 2/1986 | Manahan et al. |
| 4,570,478 A | 2/1986 | Soong |

(List continued on next page.)

FOREIGN PATENT DOCUMENTS

| | | |
|---|---|---|
| EP | 0 317 356 A2 | 5/1989 |
| JP | 402297040 A | 12/1990 |
| WO | WO 96/11878 | 4/1996 |
| WO | WO 98/15501 | 4/1998 |
| WO | WO 99/18431 | 4/1999 |
| WO | WO 00/17413 | 3/2000 |
| WO | WO 00/23921 | 4/2000 |
| WO | WO 00/36410 | 6/2000 |
| WO | WO 00/40331 | 7/2000 |
| WO | WO 00/51720 | 9/2000 |
| WO | WO 00/67086 | 11/2000 |
| WO | WO 01/79949 A2 | 10/2001 |

OTHER PUBLICATIONS

U.S. patent application Ser. No. 09/939,404 entitled "High Throughput Mechanical Property and Bulge Testing of Material Libraries," (D. Hajduk et al.) filed on Aug. 24, 2001.

(List continued on next page.)

Primary Examiner—Edward Lefkowitz
Assistant Examiner—Corey D. Mack
(74) Attorney, Agent, or Firm—Dobrusin & Thennisch PC

(57) ABSTRACT

A library of materials is screened for mechanical properties such as strength, tack, frictional resistance or other properties. A library of materials is provided. A stimulus such as a stress or force is provided to each member of the library. A response (e.g., a strain) of each of the materials due to the stimulus is measured and the response, the stimulus or both are recorded and related to provide data. Thereafter, the data is analyzed to reach conclusions regarding properties of the material samples.

21 Claims, 17 Drawing Sheets

U.S. PATENT DOCUMENTS

| | | |
|---|---|---|
| 4,599,219 A | 7/1986 | Cooper et al. |
| 4,602,501 A | 7/1986 | Hirata |
| 4,605,589 A | 8/1986 | Orphanides |
| 4,680,958 A | 7/1987 | Ruelle et al. |
| 4,685,328 A | 8/1987 | Huebner et al. |
| 4,699,000 A | 10/1987 | Lashmore et al. |
| 4,715,007 A | 12/1987 | Fujita et al. |
| 4,740,078 A | 4/1988 | Daendliker et al. |
| 4,749,854 A | 6/1988 | Martens |
| 4,789,236 A | 12/1988 | Hodor et al. |
| 4,793,174 A | 12/1988 | Yau |
| 4,829,837 A | 5/1989 | Telfer |
| 4,893,500 A | 1/1990 | Fink-Jensen |
| 4,899,575 A | 2/1990 | Chu et al. |
| 4,899,581 A | 2/1990 | Allen et al. |
| 4,932,270 A | 6/1990 | Lurie et al. |
| 4,975,320 A | 12/1990 | Goldstein et al. |
| 5,008,081 A | 4/1991 | Blau et al. |
| 5,051,239 A | 9/1991 | von der Goltz |
| 5,092,179 A | 3/1992 | Ferguson |
| 5,115,669 A | 5/1992 | Fuller et al. |
| 5,142,900 A | 9/1992 | Duke |
| 5,193,383 A | 3/1993 | Burnham et al. |
| 5,236,998 A | 8/1993 | Lundeen et al. |
| 5,269,190 A | 12/1993 | Kramer et al. |
| 5,271,266 A | 12/1993 | Eschbach |
| 5,272,912 A | 12/1993 | Katsuzaki |
| 5,280,717 A | 1/1994 | Hoseney et al. |
| 5,303,030 A | 4/1994 | Abraham et al. |
| 5,305,633 A | 4/1994 | Weissenbacher et al. |
| 5,398,885 A | 3/1995 | Andersson et al. |
| 5,437,192 A | 8/1995 | Kawamoto et al. |
| 5,438,863 A | 8/1995 | Johnson |
| 5,452,614 A | 9/1995 | Kato et al. |
| 5,452,619 A | 9/1995 | Kawanabe et al. |
| 5,481,153 A | 1/1996 | Turner |
| 5,517,860 A | 5/1996 | Lin et al. |
| 5,520,042 A | 5/1996 | Garritano et al. |
| 5,532,942 A | 7/1996 | Kitamura et al. |
| 5,610,325 A | 3/1997 | Rajagopal et al. |
| 5,626,779 A | 5/1997 | Okada |
| 5,699,159 A | 12/1997 | Mason |
| 5,700,953 A | 12/1997 | Hlady et al. |
| 5,723,792 A | 3/1998 | Miyazaki |
| 5,728,532 A | 3/1998 | Ackley |
| 5,756,883 A | 5/1998 | Forbes |
| 5,764,068 A | 6/1998 | Katz et al. |
| 5,776,359 A | 7/1998 | Schultz et al. |
| 5,817,947 A | 10/1998 | Bergerus |
| 5,821,407 A | 10/1998 | Sekiguchi et al. |
| 5,847,283 A | 12/1998 | Finot et al. |
| 5,877,428 A | 3/1999 | Scolton |
| 5,892,157 A | 4/1999 | Syre |
| 5,922,967 A | 7/1999 | Motoyama |
| 5,959,297 A | 9/1999 | Weinberg et al. |
| 5,985,356 A | 11/1999 | Schultz et al. |
| 5,999,887 A | 12/1999 | Giannakopoulos et al. |
| 6,004,617 A | 12/1999 | Schultz et al. |
| 6,010,616 A | 1/2000 | Lewis et al. |
| 6,013,199 A | 1/2000 | McFarland et al. |
| 6,030,917 A | 2/2000 | Weinberg et al. |
| 6,033,913 A | 3/2000 | Morozov et al. |
| 6,034,240 A | 3/2000 | La Pointe |
| 6,034,775 A | 3/2000 | McFarland et al. |
| 6,040,193 A | 3/2000 | Winkler et al. |
| 6,043,317 A | 3/2000 | Mumick et al. |
| 6,043,363 A | 3/2000 | LaPointe et al. |
| 6,045,671 A | 4/2000 | Wu et al. |
| 6,050,138 A | 4/2000 | Lynch et al. |
| 6,050,139 A | 4/2000 | Bousfield et al. |
| 6,087,181 A | 7/2000 | Cong |
| 6,092,414 A | 7/2000 | Newman |
| 6,124,476 A | 9/2000 | Guram et al. |
| 6,149,882 A | 11/2000 | Guan et al. |
| 6,151,123 A | 11/2000 | Nielsen |
| 6,157,449 A | 12/2000 | Hajduk |
| 6,175,409 B1 | 1/2001 | Nielsen et al. |
| 6,177,528 B1 | 1/2001 | LaPointe et al. |
| 6,182,499 B1 | 2/2001 | McFarland et al. |
| 6,187,164 B1 | 2/2001 | Warren et al. |
| 6,203,726 B1 | 3/2001 | Danielson et al. |
| 6,225,487 B1 | 5/2001 | Guram |
| 6,225,550 B1 | 5/2001 | Hornbostel et al. |
| 6,230,548 B1 | 5/2001 | Han et al. |
| 6,242,623 B1 | 6/2001 | Boussie et al. |
| 6,248,540 B1 | 6/2001 | Weinberg et al. |
| 6,260,407 B1 | 7/2001 | Petro et al. |
| 6,265,226 B1 | 7/2001 | Petro et al. |
| 6,265,601 B1 | 7/2001 | Guram et al. |
| 6,268,513 B1 | 7/2001 | Guram et al. |
| 6,294,388 B1 | 9/2001 | Petro |
| 6,296,771 B1 | 10/2001 | Miroslav |
| 6,306,658 B1 | 10/2001 | Turner et al. |
| 6,315,923 B1 | 11/2001 | Devenney et al. |
| 6,326,090 B1 | 12/2001 | Schultz et al. |
| 6,336,353 B2 | 1/2002 | Matsiev et al. |
| 6,393,898 B1 | 5/2002 | Hajduk et al. |

OTHER PUBLICATIONS

U.S. patent application Ser. No. 09/939,139 entitled "High Throughput Fabric Handle Screening," (M. Kossuth et al.) filed on Aug. 24, 2001.

U.S. patent application Ser. No. 09/939,149 entitled "High Throughput Rheological Testing of Materials," (P. Mansky et al.) filed on Aug. 24, 2001).

U.S. patent application Ser. No. 09/939,263 entitled "High Throughput Mechanical Property Testing of Materials Libraries Using Capacitance," (D. Hajduk et al.) filed on Aug. 24, 2001.

U.S. patent application Ser. No. 09/938,994 entitled "High Throughput Mechanical Property Testing of Materials Libraries Using a Piezoelectric," (D. Hajduk) filed on Aug. 24, 2001.

The family of applications for U.S. patent application Ser. No. 09/580,024 entitled "Instrument for High Throughput Measurement of Material Physical Properties and Method of Using Same," (Carlson, et al.) filed on May 26, 2000.

U.S. application Ser. No. 09/801,165 entitled "Method and Apparatus for Characterizing Materials By Using a Mechanical Resonator" filed Mar. 7, 2001.

U.S. application Ser. No. 09/578,997 entitled "High Throughput Viscometer and Method of Using Same" filed May 25, 2000.

The family of applications for U.S. application Ser. No. 09/156,827 entitled "Formation of Combinatorial Arrays of Materials Using–Based Methodologies" (Giaquinta et al.) filed Sep. 18, 1998.

U.S. application Ser. No. 09/579,338 entitled "Rheo–Optical Indexer and Method of Screening and Characterizing Arrays of Materials" (Carlson et al.) filed on May 25, 2000.

U.S. application Ser. No. 09/420,334 entitled "Graphic Design of Combinatorial Material Libraries" (Lacy, et al.) filed on Oct. 18, 1999.

U.S. patent application Ser. No. 09/305,830 titled "Synthesizing Combinatorial Libraries of Materials" (Rust, et al.) filed on May 5, 1999.

U.S. application Ser. No. 09/550,549 entitled "Automated Process Control And Data Management System And Methods" (Crevier, et al.) filed on Apr. 14, 2000.

U.S. application Ser. No. 09/755,623 entitled "Laboratory Database System and Methods For Combinatorial Materials Research" (Dorsett, Jr., et al.) filed on Jan. 5, 2001.

The family of applications for U.S. application Ser. No. 09/227,558 entitled, "Apparatus and Method of Research for Creating and Testing Novel Catalysts, Reactions and Polymers" (Turner et al.) filed Jan. 8, 1999.

U.S. application Ser. No. 09/235,368 entitled "Polymerization Method From the Combinatorial Synthesis and Analysis of Organometallic Compounds and Catalysts" (Weinberg et al.) filed on Jan. 21, 1999.

U.S. Provisional application Ser. No. 60/122,704 entitled "Controlled, Stable Free Radical Emulsion and Water–Based Polymerizations" (Klaerner et al.) filed on Mar. 9, 1999.

The family of applications for U.S. application Ser. No. 09/567,598 entitled "Polymer Libraries on a Substrate, Method for Forming Polymer Libraries on a Substrate and Characterization Methods with Same" (Boussie et al.) filed May 10, 2000.

The family of applications for U.S. patent application Ser. No. 09/174,856 titled "Graphic Design of Combinatorial Material Libraries" (Lacy, et al.) filed on Oct. 19, 1998.

Young, W.C., Roark's Formulas for Stress and Stain, 1989.

Osterberg, Peter M. and Stephen D. Senturia, "M–TEST: A Test Chip for MEMS Material Property Measurement Using Electrostatically Actuated Test Structures," Journal of Microelectromechanical Systmes, vol. 6, No. 2, Jun. 1997.

Kim, J.O. and B. Lewis Slaten, "Objective Assessment of Fabric Handle in Fabrics Treated With Flame Retardants," Journal of Testing and Evaluation, JTEVA, vol. 24, No. 4, Jul. 1996, pp. 223–228.

Grover, G. et al., "A Screening Technique for Fabric Handle", J. Text. Inst., 1993, 84 No. J. Textile Institute, pp. 486–494.

Pan, Ning and K.C. Yen, "Physical Interpretations of Curves Obtained Through the Fabric Extraction Process for Handle Measurement," Textile Research Journal 62(5), pp. 279–290 (1992).

"Handle–O–Meter", Thwing–Albert Instrument Company, Philadelphia, PA.

Raeel, Mastura and Jiang Liu, "An Empirical Model for Fabric Hand"Textile Research Journal 62, 1, pp. 31–38 (1991).

Ali, S.I. and Shahida Begum, "Fabric Softeners and Softness Perception", Ergonomics, v.37, No. 5, pp. 801–806 (1994).

Odian, Principles of Polymerization, 3rd Ed., John Wiley & Sons, Inc. (1991).

Timoshenko, S., Theory of Plates and Shells, McGraw–Hill, New York 1940.

"DMA 2980 Dynamic Mechanical Analyer," http://www.tainst.com/dma2.html, Dec. 29, 2000.

"Introducing the New DMTA V!", http://www.rheometric-scientific.com/dmtaV.htm, Dec. 29, 2000.

"Standard Test Method for Rubber Property–International Hardness," American Society for Testing and Materials.

Amitay–Sadovsky, Ella and H. Daniel Wagner, "Evaluation of Young's Modulus of Polymers from Knoop Microindentation Tests" Polymer Communications, 1998, vol. 39, No. 11, pp. 2387–2390.

Calleja, F.J. Balta, "Microhardness Studies of Polymers and Their Transitions" TRIP, Dec. 1994, vol. 2, No. 12, pp. 419–425.

Bowlt, C., "A Simple Capillary Viscometer" Physics Education, Mar. 1975, vol. 10, No. 2, pp. 102–103.

Lacombe, Robert H. and Jeremy Greenblatt, "Mechanical Propoerties of Thin Polyimide Films" pp. 647–668.

Shinozaki, D.M. and Y. Lu, "Micro–Indentation Relaxation Measurements in Polymer Thin Films" Journal of Electronic Materials, 1997, vol. 26, No. 7, pp. 852–858.

Wierenga, P.E. and A.J.J. Franken, "Ultramicroindentation Apparatus for the Mechanical Characterization of Thin Films" J. Appl. Phys., Jun. 15, 1984, 55 (12).

European Search Report dated Dec. 10, 2001.

U.S. patent application Ser. No. 02/019,4930, Crosby et al., filed Dec. 26, 2002.

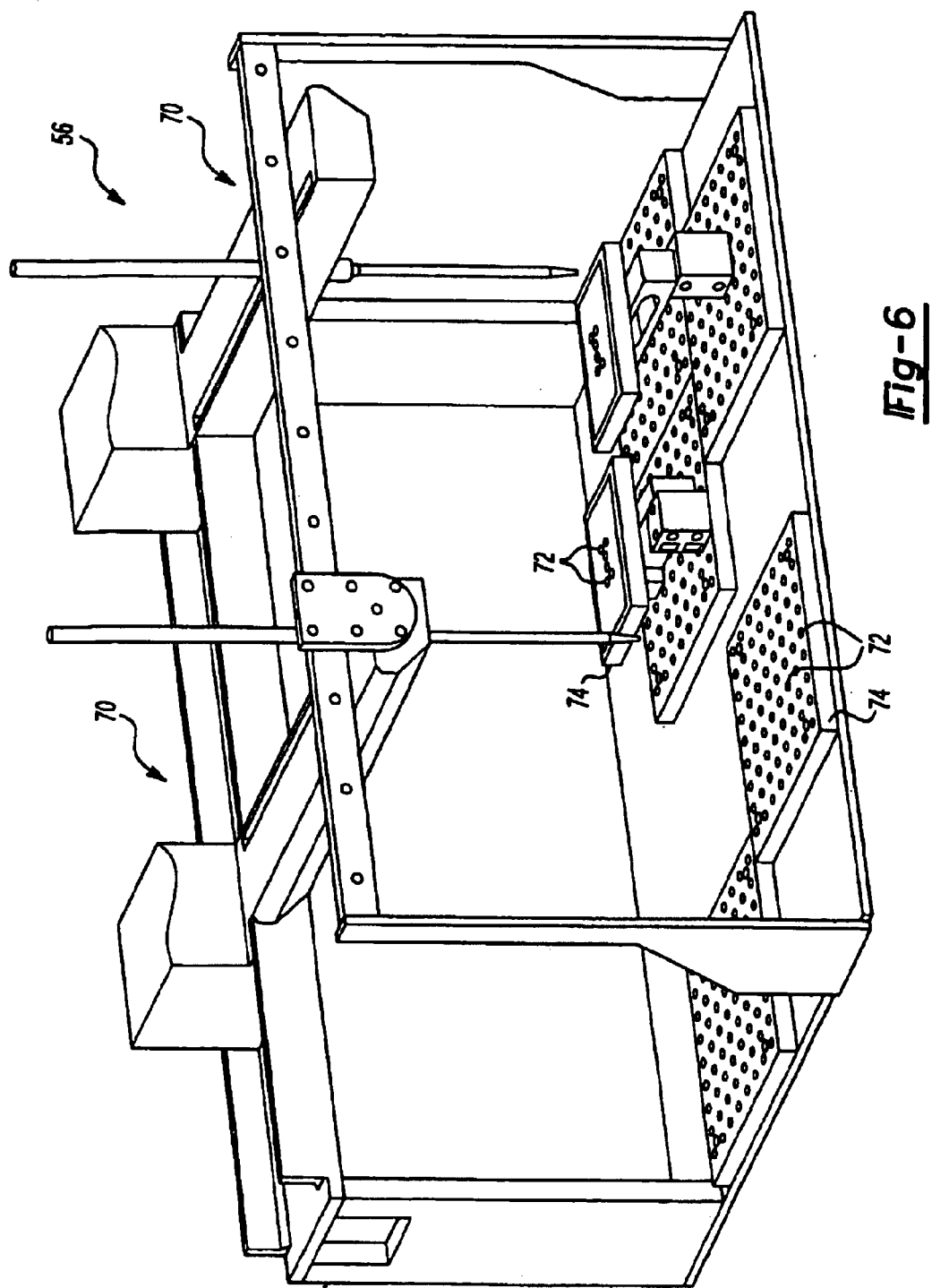

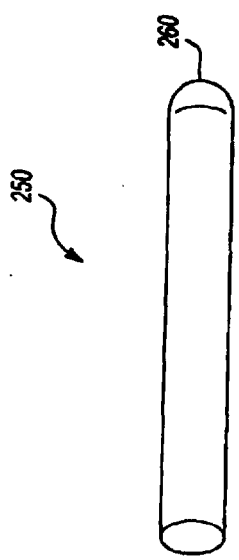
Fig-7A
Fig-7B
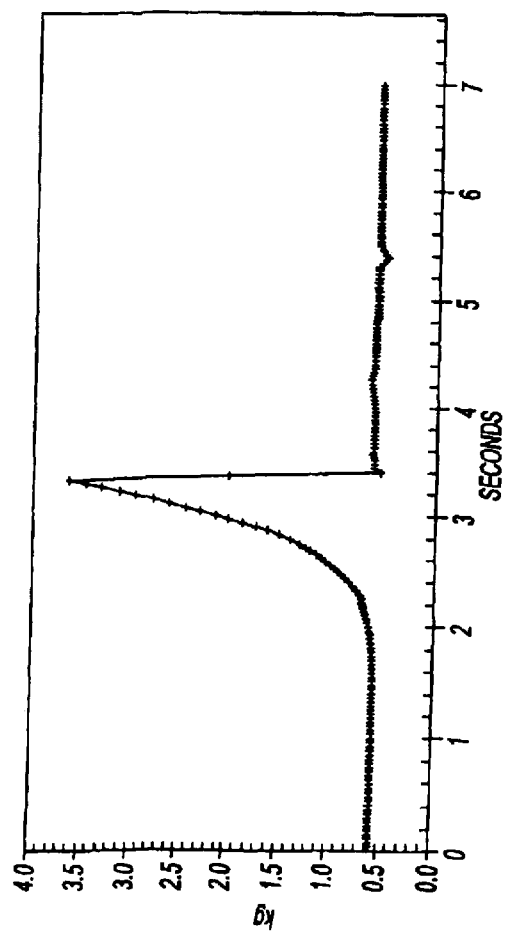
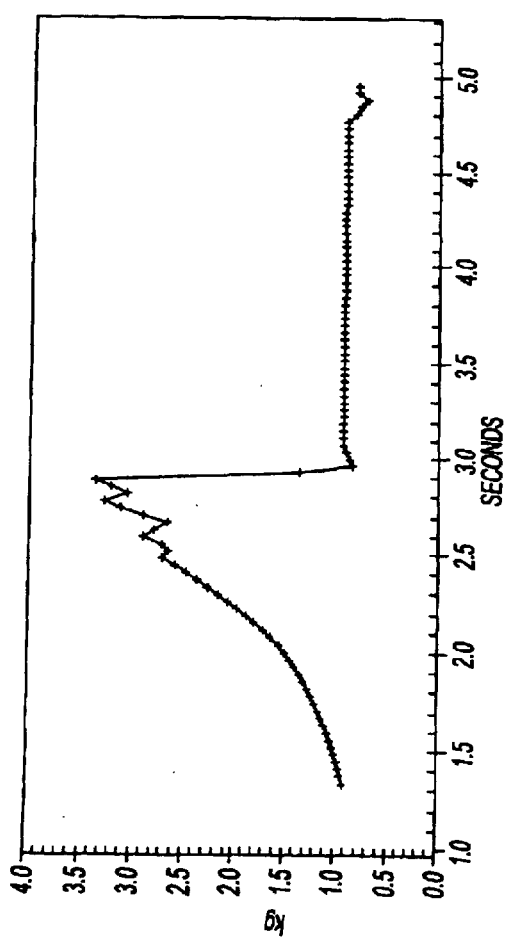

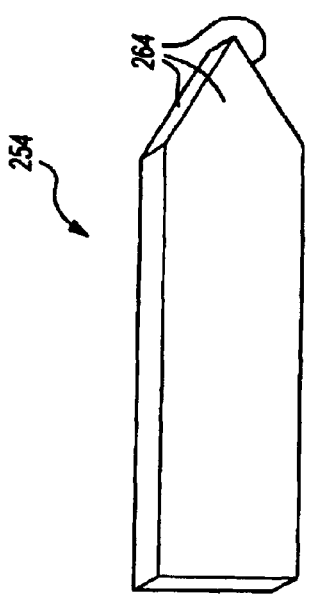
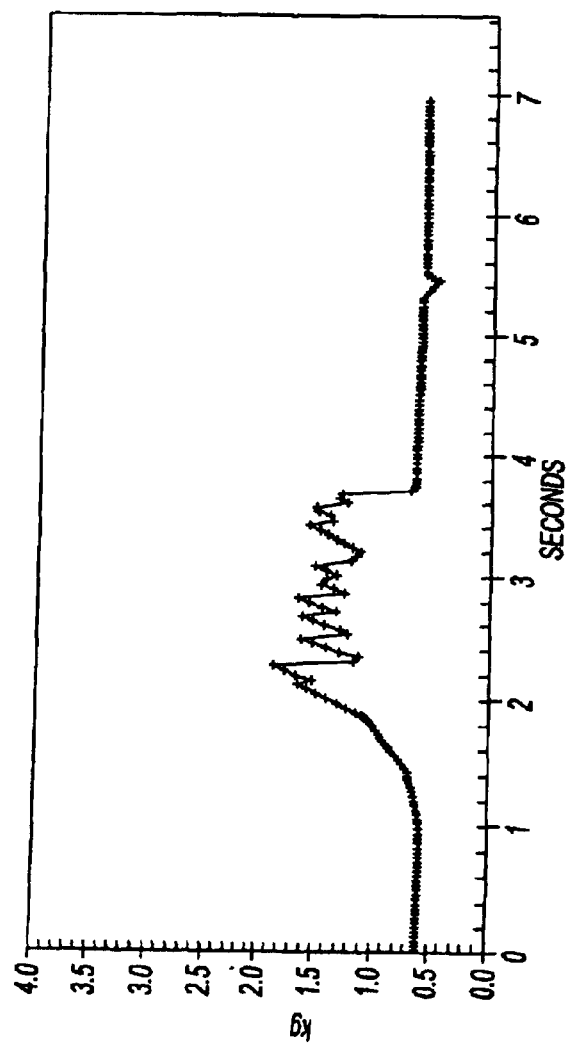
Fig-7C

Fig-12D  Fig-12E
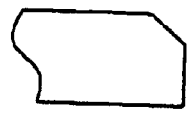
Fig-12F  Fig-12G
Fig-12H  Fig-12I
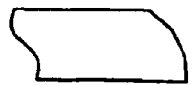
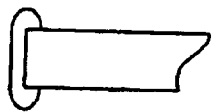
Fig-12J

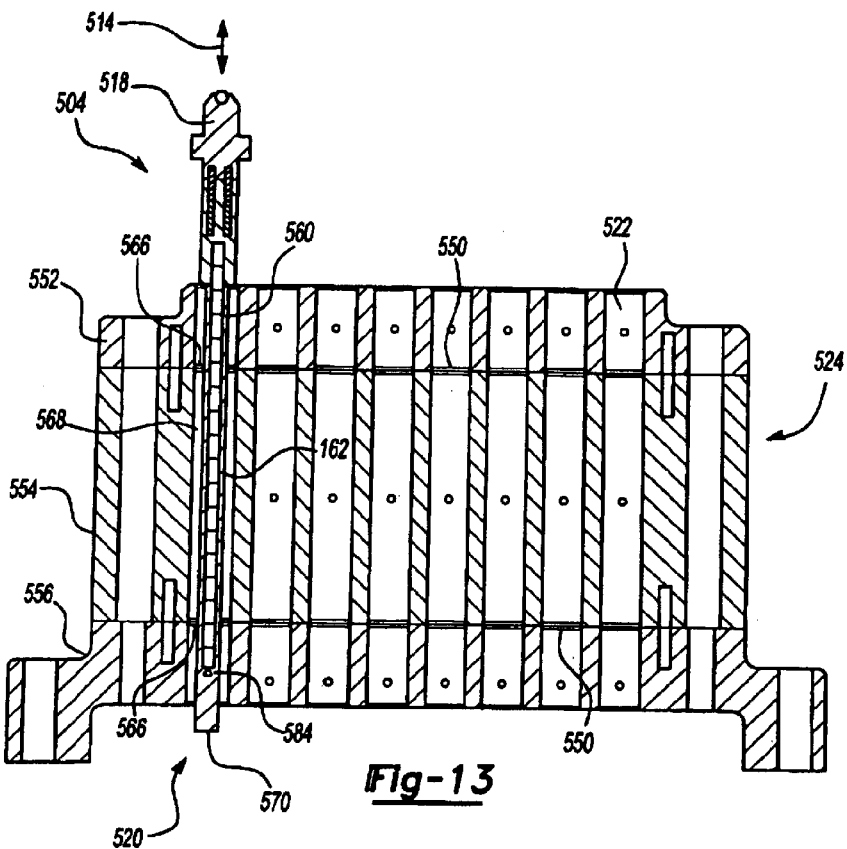
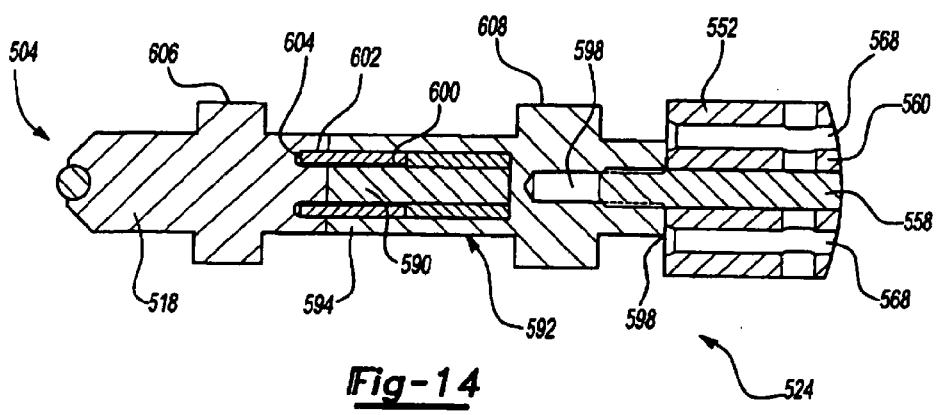

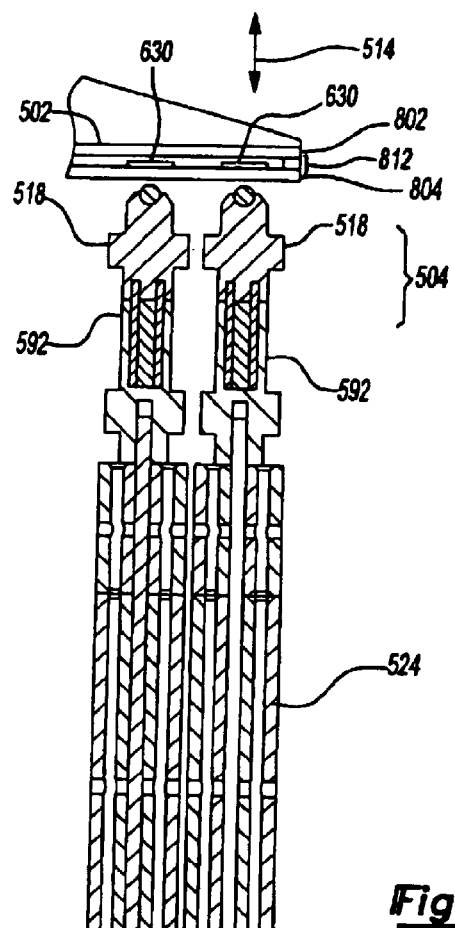
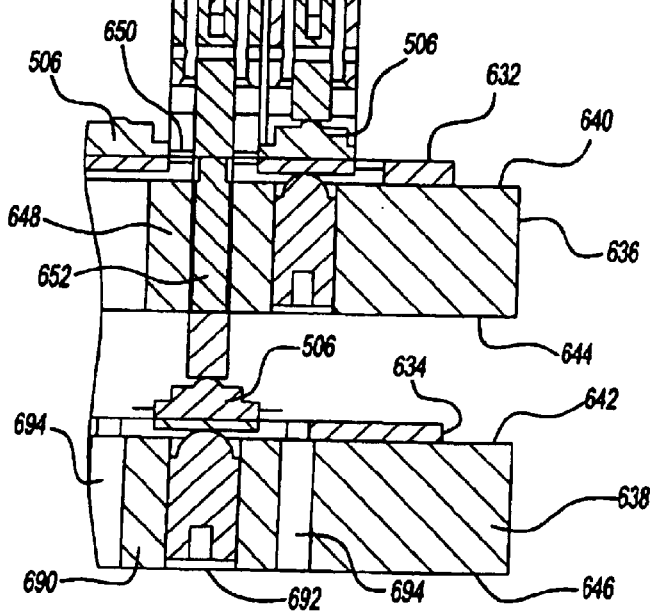
Fig-15

HIGH THROUGHPUT MECHANICAL RAPID SERIAL PROPERTY TESTING OF MATERIALS LIBRARIES

CROSS-REFERENCE

This application is a continuation-in-part of U.S. application Ser. No. 09/939,252, filed Aug. 24, 2001 and a continuation-in-part of U.S. application Ser. No. 09/939,139, also filed Aug. 24, 2001.

TECHNICAL FIELD

The present invention generally relates to the field of materials characterization or materials testing. In particular, the invention relates to high throughput rapid serial screens for evaluating properties such as, strength, tack, adhesiveness, frictional resistance and the like of libraries of polymers or other materials.

BACKGROUND OF THE INVENTION

Currently, there is substantial research activity directed toward the discovery and optimization of materials for a wide range of applications. Although the chemistry of many materials, including polymers and polymerization reactions has been extensively studied, nonetheless, it is rarely possible to predict a priori the physical or chemical properties a particular material will possess or the precise composition and architecture that will result from any particular synthesis scheme. Thus, characterization or testing techniques to determine such properties are an essential part of the discovery process.

Combinatorial materials science refers generally to methods for synthesizing a collection of chemically diverse materials and to methods for rapidly testing or screening this collection of materials for desirable performance characteristics and properties. Combinatorial chemistry approaches have greatly improved the efficiency of discovery of useful materials. For example, material scientists have developed and applied combinatorial chemistry approaches to discover a variety of novel materials, including for example, high temperature superconductors, magnetoresistors, phosphors and catalysts. See, for example, U.S. Pat. No. 5,776,359 to Schultz et al. In comparison to traditional materials science research, combinatorial materials research can effectively evaluate much larger numbers of diverse compounds in a much shorter period of time. Although such high-throughput synthesis and screening methodologies are conceptually promising, substantial technical challenges exist for application thereof to specific research and commercial goals.

The characterization or testing of polymers or other materials using combinatorial methods has only recently become known. Examples of such technology are disclosed, for example, in commonly owned U.S. Pat. No. 6,182,499 (McFarland et al); U.S. Pat. No. 6,175,409 B1 (Nielsen et al); U.S. Pat. No. 6,157,449 (Hajduk et al); U.S. Pat. No. 6,151,123 (Nielsen); U.S. Pat. No. 6,034,775 (McFarland et al); U.S. Pat. No. 5,959,297 (Weinberg et al), all of which are hereby expressly incorporated by reference herein. However, as combinatorial materials science becomes more accepted, a need exists to rapidly test or characterize a wider variety of properties. The above-cited references do not disclose every possible test that might be performed in the research and development of materials for a specific desired application.

For example, a need exists for combinatorial methods and apparatuses for synthesizing or otherwise providing polymers and other materials in an array format followed by screening of those materials for physical or mechanical characteristics such as strength, elasticity, tack, adhesiveness and the like. Conventional instruments and methods for synthesis and screening of the materials for mechanical properties are generally inadequate to handle the types and numbers of samples. For example, conventional instruments, such as conventional stress or strain testing machines and other instruments lack the ability to screen mechanical properties of several materials in rapid succession, in parallel, on a single substrate or a combination thereof. Conventional instruments also typically require a sample that is of sufficient size for bulk properties to be measured by the sensor of the instrument. High-throughput or combinatorial samples tend to be smaller and more numerous, requiring new methods to handle the volume and sensitivity needed. Thus, challenges are presented for creating systems and methods that can quickly process and test (either in parallel or in serial succession) mechanical properties of many materials. Additionally, combinatorial or high-throughput methods that create material sample must be processed at a similar rate and conventional instruments are inadequate for forming, processing or otherwise treating materials so that the materials are in appropriate condition for high throughput screening of mechanical properties. This invention meets these challenges and the inadequacies of the prior art for certain properties of materials.

SUMMARY OF THE INVENTION

In accordance with one preferred embodiment of the present invention, a method for screening an array of materials for strength is provided. According to the method a library of at least four sample materials is provided. One or more forces is applied to each of the at least four sample materials with one or more probes wherein the one or more probes are moved by an automatic system for applying the one or more forces. A sample response is monitored. Preferably, the response of each of the at least four sample materials is further correlated to assess strength (absolute, relative or both) of each of the at least four sample materials.

In accordance with another preferred embodiment of the present invention, a method for screening an array of materials for one or more adhesive properties is provided. According to the method a library of at least four sample materials is provided. Each of the at least four sample materials is contacted with at least one member for applying one or more forces to the at least four sample materials in opposition to the one or more adhesive properties of the at least four sample materials wherein the at least one member is moved by an automatic system for applying the one or more forces. A response is monitored. Preferably, the response of the each of the at least four sample materials is further correlated to assess the one or more adhesive properties of the each of the at least four sample materials.

In accordance with one preferred embodiment of the present invention, a method for screening an array of materials for frictional resistance is provided. According to the method a library of at least four sample materials is provided. One or more forces is applied to each of the at least four sample materials with one or more probes wherein the one or more probes are moved by an automatic system for applying the one or more forces. A sample response is monitored. Preferably, the response of each of the at least four sample materials is further correlated to assess frictional resistance of each of the at least four sample materials.

In accordance with another preferred embodiment of the present invention, there are provided methods for high throughput fabric handle screening that address many of the challenges encountered when using conventional methods and instruments. For example, the disclosed methods can screen for the mechanical properties associated with fabric handle of an array of fabric samples in parallel and/or rapid serial and can perform screens on small samples of fabric materials. Thus, the present invention provides methods of screening the mechanical properties associated with fabric handle of a plurality of fabric samples (e.g., assembled together in an array).

In accordance with another preferred embodiment of the present invention, a method for measuring strength of a plurality of sample materials is provided. According to the method, a library comprising at least four different sample materials is provided. Thereafter, the strength of each of the at least four sample materials is measured at a throughput rate no greater than about 5 minutes per sample material.

In accordance with yet another preferred embodiment of the present invention, a method for measuring an adhesive property of a plurality of sample materials is provided. According to the method a library comprising at least four different sample materials is provided. Thereafter, the adhesive property of each of the at least four different sample materials is measured at a throughput rate no greater than about 5 minutes per sample material.

In another aspect, two or more of the above-described embodiments of this invention can be combined into a system that measures the properties of the sample materials disclosed in that embodiment. Combination of the embodiments allows for more comprehensive property analysis of the sample materials in a single testing regime.

BRIEF DESCRIPTION OF THE DRAWINGS

FIG. 6 is an exemplary automated apparatus or system for assisting in determining mechanical properties in accordance with the present invention.

FIGS. 7(a)–7(c) illustrate probes of the present invention.

FIGS. 12C–J each shows a cross sectional view of an opening for which an array sample is protruded through during high throughput fabric handle screening.

FIG. 13 shows a cross sectional view of an isolation block module that separates the probe test fixtures and the array of fabric samples from the force sensors in a parallel dynamic mechanical analyzer.

FIG. 14 shows a close-up cross sectional view of the probe shown in FIG. 4, and illustrates the use of a permanent magnet to attach the test fixture to the threaded cylindrical core of the composite shaft.

FIG. 15 shows a cross sectional view of two adjacent isolation block modules, and illustrates interactions of probes and force sensors in a parallel dynamic mechanical analyzer.

DETAILED DESCRIPTION OF THE PREFERRED EMBODIMENT

I. Glossary

The following terms are intended to have the following general meanings as they are used herein.

1. Mixture: The term "mixture" refers to a collection of molecules, ions, electrons, chemical substances, etc. Each component in the mixture can be independently varied. A mixture can consist of two or more substances intermingled with no constant percentage composition, wherein each component may or may not retain its essential original properties, and where molecular phase mixing may or may not occur. In mixtures, the components making up the mixture may or may not remain distinguishable from each other by virtue of their chemical structure.

2. Adhesiveness or adhesive property: A measure of the tendency or ability of a material such as a sealant to adhesively secure itself or stick to one or more objects. The adhesiveness of a material may be due to bonding (chemical or otherwise) of the material to an object, electrostatic attraction of a material to an object or any other phenomenon that allows a material to secure itself to another object due at least in part to the natural characteristics or properties of the material. The term tack as used herein is considered to be an adhesive property. Also, as used herein, without limitation, adhesiveness may be defined by the deformation of an adhesive material due to a force applied against the adhesiveness of the material or by the amount of force acting against the adhesiveness of a material or by any other quantification that assists in defining the ability of a material to adhere itself to another object.

3. Strength: Generally strength, as used herein, relates to the ability of a material to resist a force, stress, strain or a combination thereof. Strength, as used herein, can mean any of these resistances and may be quantified or defined in terms of force, force per unit area, stress, strain and the like. Moreover, strength may be used generally to include any properties or quantifications related to the strength of a material. Examples of such properties or quantifications include, without limitation, moduli such as moduli of elasticity, young's modulus, shear modulus and the like, failure modes such as ultimate strength or other properties or quantifications related to strength. As used herein, the term "protrusions" generally refers to controlled forces or displacements applied by a probe, or device to a fabric sample for causing at least a portion of the fabric sample to be forced through an opening defined in a plane of a sample support member. Preferably a protrusion as used herein will be of sufficient magnitude for effecting such sample manipulation without piercing the sample. In some embodiments, however, it is contemplated that piercing will or desirably should occur.

Figure 1:
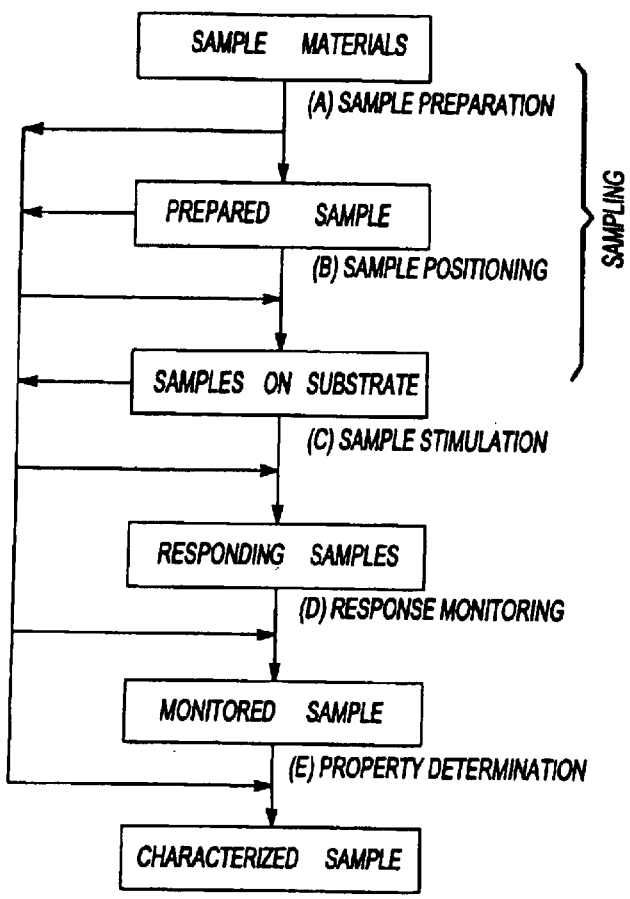
FIG. 1 is a flowchart of possible steps for methods of the present invention.

In accordance with effectuating one type of preferred protrusion, as the sample is passed through the opening (i.e., pushed out of the normal plane of the opening), it is expected to become folded, sheared, bent, compressed, elongated, or rubbed against the interior wall of the support member defining the opening. Responses to the protrusions are measured and recorded as a load-displacement curve as shown in FIG. 1. The load displacement curve yields the mechanical properties associated with or bearing upon fabric handle such as bending modulus, shear stiffness, compression, friction, and extensibility, or the like.

These and other aspects of the invention are to be considered exemplary and non-limiting, and are discussed in greater detail below. The several aspects of the characterization methods and systems disclosed and claimed herein can be advantageously employed separately, or in combination to efficiently characterize a variety of materials, with particular emphasis on solid materials, polymeric materials, liquid materials or flowable materials. In preferred embodiments, these features are employed in combination to form a materials characterization system that can operate as a high-throughput screen in a combinatorial materials science research program directed to identifying and optimizing new materials. Such materials appropriate for combinatorial research may include, for instance, polymers, catalysts, products of various polymerization reaction conditions, lubricants, gels, adhesives, coatings and/or products of new post-synthesis processing conditions. Other materials appropriate for combinatorial research according to the present invention may include, but are not limited to, foodstuffs, cosmetics, beverages, lotions, creams, pharmaceuticals, inks, mucus, fuels, additives, detergents, surfactants, shampoos, conditioners, dyes, waxes, fuel cell electrolytes, photoresist, semiconductor material, wire coatings, hair styling products and the like.

Combinatorial Approaches for Science Research

In a combinatorial approach for identifying or optimizing materials or reactions, a large compositional space (e.g., in the context of polymers; of monomers, comonomers, catalysts, catalyst precursors, solvents, initiators, additives, or of relative ratios of two or more of the aforementioned) or a large reaction condition space (e.g., of temperature, pressure and reaction time) may be rapidly explored by preparing libraries and then rapidly screening such libraries.

For example, in the context of polymers (but also applicable to other materials), combinatorial approaches for screening a material or polymer library can include an initial, primary screening, in which polymerization products are rapidly evaluated to provide valuable preliminary data and, optimally, to identify several "hits"—particular candidate materials having characteristics that meet or exceed certain predetermined metrics (e.g., performance characteristics, desirable properties, unexpected and/or unusual properties, etc.). Thus a screen will allow a determination of those materials that should pass through to additional testing.

Once one or more hits have been satisfactorily identified based on the primary screening, optionally, material or polymer and polymerization product libraries focused around the primary-screen hits can be synthesized and/or evaluated with a secondary screen—a screen designed to provide (and typically verified, based on known materials, to provide) chemical composition or process conditions that relate with a greater degree of confidence to commercially-important processes and conditions than those applied in the primary screen.

In general, the systems, devices and methods of the present invention may be applied as either a primary, secondary or other screen, depending on the specific research program and goals thereof. Bulk quantities of a particular material may be made after a primary screen, a secondary screen, or both.

Referring to FIG. 1, the systems and methods, preferably, start with a library or array of sample materials that may exhibit one or more predetermined physical/mechanical properties. Ultimately, these predetermined properties will be determined in a determination step (Step E), however, several prior steps may be effected prior to Step E. The sample materials may be prepared such as by heating, cooling, or addition of additives. Such preparation is typically designed to affect the properties that are ultimately being determined. The sample materials may also be positioned in a desirable manner for property determination. The materials may be positioned on a substrate, a machine or otherwise positioned to assist in ultimately determining properties of the materials.

It will be appreciated that one of the advantageous features of the present invention is that it affords the ability to screen newly created materials some or all of which are uncharacterized or whose properties are unknown prior to the time of screening. Thus, previously unidentified and uncharacterized new materials can be screened for a common selected property. However, this does not prevent the employment of known references controls or standard as among the library members.

It shall be recognized that sample preparation (Step A) and sample positioning (Step B) may be optional steps in property determination protocols. Also sample preparation and sample positioning may be performed in any order if they are performed. Additionally it should be recognized that sequences other than the order of steps listed above are possible, and the above listing is not intended as limiting.

Typically, however, stimulation of the sample materials (Step C) is needed to effect one or more responses of the materials wherein the responses are related to the one or more physical properties that are being tested. Exemplary stimuli include force, contact, motion and the like. Exemplary responses include flow, or resistance to flow, deflection, adhesion, deformation, rupture or the like. Negative forces (e.g., compression as opposed to tension, negative pressure as opposed to positive pressure) or the like may be employed.

The responses of the materials are typically monitored (Step D) with hardware such as sensors, transducers, load cells or other like devices. Properties may be determined (Step E) quantitatively or qualitatively by relating the responses to the material properties.

A plurality of samples may be characterized as described above in connection with FIG. 1. As a general approach for improving the sample throughput for a plurality of samples, each of the steps (A) through (E) of FIG. 1 applicable to a given characterization protocol can be optimized with respect to time and quality of information, both individually and in combination with each other. Additionally or alternatively, each or some of such steps can be effected in a rapid-serial, parallel, serial-parallel or hybrid parallel-serial manner.

A characterization protocol for a plurality of samples can involve a single-step process (e.g., direct measurement of a property of a sample or of a component thereof) or several steps. In a rapid-serial screen approach for a single-step process, the plurality of samples and a single measuring instrument or other instruments are serially positioned in relation to each other for serial analysis of the samples. In a parallel analysis approach, (e.g., as might be employed by itself, or in an upstream or downstream analysis of the samples relative to a rapid-serial analysis of the present invention) two or more measuring instruments or other apparatus are employed to measure properties of two or more samples simultaneously.

In a serial-parallel approach, a property of a larger number of samples (e.g., four or more) is screened as follows. First, a property of a subset of the four or more samples (e.g., 2 samples) is screened in parallel for the subset of samples, and then serially thereafter, a property of another subset of four or more samples is screened in parallel. It will be recognized, of course, that plural measuring instruments can be employed simultaneous, or plural measuring instruments can be employed serially.

In a hybrid approach, certain of the steps of the characterization process can be effected in parallel, while certain other steps can be effected in series. Preferably, for example, it may be desirable to effect the longer, throughput-limiting steps in parallel for the plurality of samples, while effecting the faster, less limiting steps in series.

Sample Materials

The samples for which the present invention is useful for screening include polymeric materials or any other liquid, flowable or solid material that is capable of being provided as a liquid, solid, paste, cream, gel or other suitable form. Accordingly, without limitation, pure materials, mixtures of materials, bulk materials, particles of materials, thin films of materials, dispersions of materials, emulsions of materials, and solutions of materials are all contemplated as within the useful scope of the present invention.

In a particularly preferred embodiment, the present invention is employed for screening polymer samples, or plastic samples including polymers.

In one embodiment, the polymer molecule of the polymer component is preferably, but need not be, a non-biological polymer. A non-biological polymer is, for purposes herein, a polymer other than an amino-acid polymer (e.g., protein) or a nucleic acid polymer (e.g., deoxyribonucleic acid (DNA)). However, the employment of the present invention for screening of materials for use as biological implants or prosthetics is contemplated. For instance, the ability of a biological polymer to bind to an agent may be determined from the mechanical property response of a sample of the material in the presence of such agent.

The particular composition of the polymer molecule is not critical. The material may be thermoplastic, thermoset or a mixture thereof. It may be a polycondensate, polyadduct, a modified natural polymer. Exemplary materials include polymers incorporating olefins, styrenes, acrylates, methacrylates, polyimides, polyamides, epoxies, silicones, phenolics, rubbers, halogenated polymers, polycarbonates, polyketones, urethanes, polyesters, silanes, sulfones, allyls, polyphenylene oxides, terphthalates, or mixtures thereof. Other specific illustrative examples can include repeat units or random occurrences of one or more of the following, without limitation: polyethylene, polypropylene, polystyrene, polyolefin, polyamide, polyimide, polyisobutylene, polyacrylonitrile, poly(vinyl chloride), poly(methyl methacrylate), poly(vinyl acetate), poly (vinylidene chloride), polytetrafluoroethylene, polyisoprene, polyacrylamide, polyacrylic acid, polyacrylate, poly(ethylene oxide), poly(ethyleneimine), polyamide, polyester, polyurethane, polysiloxane, polyether, polyphosphazine, polymethacrylate, and polyacetals. Polysaccharides are also preferably included within the scope of polymers. Exemplary naturally-occurring polysaccharides include cellulose, dextran, gums (e.g., guar gum, locust bean gum, tamarind xyloglucan, pullulan), and other naturally-occurring biomass. Exemplary semi-synthetic polysaccharides having industrial applications include cellulose diacetate, cellulose triacetate, acylated cellulose, carboxymethyl cellulose and hydroxypropyl cellulose. In any case, such naturally-occurring and semi-synthetic polysaccharides can be modified by reactions such as hydrolysis, esterification, alkylation, or by other reactions. The screening, however, should measure the properties of the material samples as they would occur in bulk production.

The polymer samples can, in any case, also include other components, such as catalysts, catalyst precursors (e.g., ligands, metal-precursors), solvents, initiators, additives, products of undesired side-reactions (e.g., polymer gel, or undesired homopolymer or copolymers) and/or impurities. Typical additives include, for example, surfactants, fillers, reinforcements, flame retardants, colorants, environmental protectants, other performance modifiers, control agents, plasticizers, cosolvents and/or accelerators, among others. In this regard, the present invention is particularly attractive for the screening of effects of variations of additives upon the characteristics of the material. The various components of the heterogeneous polymer sample can be uniformly or non-uniformly dispersed in the continuous fluid phase.

In one preferred embodiment, the polymer samples of the present invention are melted or otherwise heated to a fluid state, with the resulting material constituting a liquid sample. Heating may be performed simultaneously while the samples are on a common substrate. Alternatively, the samples might be heated to a liquid state and then transferred (e.g., manually or with an automated sampler) to a common substrate, where it is heated to maintain its liquid state.

In another embodiment at a point prior to, during, or after depositing the sample onto the substrate, the polymer sample is preferably, chemically treated to form a liquid polymer sample, such as a polymer solution, a polymer emulsion, a polymer dispersion or a polymer that is liquid in the pure state (i.e., a neat polymer). A polymer solution comprises one or more polymer components dissolved in a solvent. The polymer solution can be of a form that includes well-dissolved chains and/or dissolved aggregated micelles. The solvent can vary, depending on the application, for example with respect to polarity, volatility, stability, and/or inertness or reactivity. Typical solvents include, for example, tetrahydrofuran (THF), toluene, hexane, ethers, trichlorobenzene, dichlorobenzene, dimethylformamide, water, aqueous buffers, alcohols, etc. According to traditional chemistry conventions, a polymer emulsion can be considered to comprise one or more liquid-phase polymer components emulsified (uniformly or non-uniformly) in a liquid continuous phase, and a polymer dispersion can be considered to comprise solid particles of one or more polymer components dispersed (uniformly or non-uniformly) in a liquid continuous phase. The polymer emulsion and the polymer dispersion can also be considered, however, to have the more typically employed meanings specific to the art of polymer science—of being a emulsion-polymerization product and dispersion-polymerization product, respectively. In such cases, for example, the emulsion polymer sample can more generally include one or more polymer components that are insoluble, but uniformly dispersed, in a continuous phase, with typical emulsions including polymer component particles ranging in diameter from about 1 nm to about 500 nm, more typically from about 5 nm to about 300 nm, and even more typically from about 40 nm to about 200 nm. The dispersion polymer sample can, in such cases, generally include polymer component particles that are dispersed (uniformly or nonuniformly) in a continuous phase, with typical particles having a diameter ranging from about 0.2 um to about 1000 um, more typically from about 0.4 um to about 500 um, and even more typically from about 0.5 um to about 200 um. Exemplary polymers that can be in the form of neat polymer samples include dendrimers, and siloxane, among others. The liquid polymer sample can also be employed in the form of a slurry, a latex, a microgel, a physical gel, or in any other form sufficient for creating an array for screening analysis as described and claimed herein. In some cases, polymer synthesis reactions (i.e., polymerizations) directly produce liquid samples. These may be bulk liquid polymers, polymer solutions, or heterogeneous liquid samples such as polymer emulsions, latices, or dispersions. In other cases, the polymer may be synthesized, stored or otherwise available for characterization in a non-liquid physical state, such as a solid state (e.g., crystalline, semicrystalline or amorphous), a glassy state or rubbery state. The polymer sample can, regardless of its particular form, have various attributes, including variations with respect to polarity, solubility and/or miscibility.

It is also possible to use polymer samples or libraries of polymer samples that were prepared previously and stored. Typically, polymer libraries can be stored with agents to ensure polymer integrity. Such storage agents include, for example, antioxidants or other agents effective for preventing cross-linking of polymer molecules during storage. Depending upon the polymerization reaction, other processing steps may also be desired, all of which are preferably automated.

It will be appreciated that in certain embodiments, a polymer sample is formed in situ on a substrate, post synthesis treated in situ on a substrate, or a combination thereof. Examples of such post synthesis treatment steps include for instance, heat treating, environmental exposure (e.g. temperature moisture, radiation, chemicals, etc.), aged, or the like.

In other preferred embodiments, polymer or other sample materials may be provided as solids or semi-solids. Such samples may be provided in a variety of geometric configurations such as blocks, cylinders, loops, films and the like. Generally, geometric configurations are selected to be appropriate for one or more tests that are to be performed upon the samples. Solid and semi-solid samples may be rigid, elastic, gelatinous or otherwise. In one preferred embodiment, samples are provided in a tacky state, and thus exhibits at least some degree of adhesiveness within the range of temperature under examination. Samples may also be specifically arranged for testing. For example, samples may be interwoven as a fabric, unwoven, machined to shape, molded to shape, cut to shape or otherwise physically manipulated for testing.

Sample Size

The sample size is not narrowly critical, and can generally vary, depending on the particular characterization protocols and systems used to analyze the sample or components thereof. However, it will be appreciated that the present invention advantageously permits for attaining reliable data with relatively small samples. Typical sample sizes can range from about 0.1 microgram to about 1 gram, more typically from about 1 microgram to about 100 milligrams, even more typically from about 5 micrograms to about 1000 micrograms, and still more typically from about 20 micrograms to about 50 micrograms.

If and when placed on a substrate for forming a library, as discussed herein with regard to sampling, the samples may be dispensed with any suitable dispensing apparatus (e.g. an automated micropipette or capillary dispenser, preferably with a heated tip). Each sample of the library is dispensed to an individually addressable region on the substrate. Preferably each sample occupies no more than about 1000 mm$^2$ of area on a substrate surface, more preferably no more than about 100 mm$^2$, and even more preferably no more than about 10 mm$^2$. In applications where the sample is disposed in a well, preferably the sample size does not exceed about 1000 milligrams.

Accordingly, for dispensing fluid samples, the individual samples are each dispensed in amounts no greater than about 100 ml, more preferably no greater than about 10 ml and still more preferably no greater than about 1 ml.

Libraries of Sample Materials

Libraries of samples have 2 or more samples that are physically or temporally separated from each other—for example, by residing in different regions of a common substrate, in different sample containers of a common substrate, by having a membrane or other partitioning material positioned between samples, or otherwise. The plurality of samples preferably has at least 4 samples and more at least 8 samples. Four samples can be employed, for example, in connection with experiments having one control sample and three polymer samples varying (e.g., with respect to composition or process conditions as discussed above) to be representative of a high, a medium and a low-value of the varied factor—and thereby, to provide some indication as to trends. Higher numbers of samples can be investigated, according to the methods of the invention, to provide additional insights into larger compositional and/or process space. In some cases, for example, the plurality of samples can be 15 or more samples, preferably 20 or more samples, more preferably 40 or more samples and even more preferably 80 or more samples. For screening of polymers or other materials the number of samples can be 150 or more, 400 or more, 500 or more, 750 or more, 1,000 or more, 1,500 or more, 2,000 or more, 5,000 or more and 10,000 or more samples. As such, the number of samples can range from about 2 samples to about 10,000 samples or more, and preferably from about 8 samples to about 10,000 or more samples. In many applications, however, the number of samples can range from about 80 samples to about 1500 samples.

A library of samples comprises two or more different samples spatially separated—preferably, but not necessarily on a common substrate, or temporally separated. Candidate samples (i.e., members) within a library may differ in a definable and typically predefined way, including with regard to chemical structure, processing (e.g., synthesis)

history, mixtures of interacting components, post-synthesis treatment, purity, etc. The samples are spatially separated, preferably at an exposed surface of the substrate, such that the library of samples is separately addressable for characterization thereof. The two or more different samples can reside in sample containers formed as wells in a surface of the substrate. The number of samples included within the library can generally be the same as the number of samples included within the plurality of samples, as discussed above. In general, however, not all of the samples within a library of samples need to be different samples. When process conditions are to be evaluated, the libraries may contain only one type of sample. The use of reference standards, controls or calibration standards may also be performed, though it is not necessary. Further, a library may be defined to include sub-groups of members of different libraries, or it may include combinations of plural libraries.

Typically, however, for combinatorial science research applications, at least two or more, preferably at least four or more, even more preferably eight or more and, in many cases, most preferably each of the plurality of polymer samples in a given library of samples will be different from each other. Specifically, a different sample can be included within at least about 50%, preferably at least 75%, preferably at least 80%, even more preferably at least 90%, still more preferably at least 95%, yet more preferably at least 98% and most preferably at least 99% of the samples included in the sample library. In some cases, all of the samples in a library of samples will be different from each other.

In one embodiment, preferably at least eight samples are provided in a library on a substrate and at least about 50% of the samples included in the library are different from each other. More preferably, the library includes at least 16 samples and at least 75% of said samples included in said library are different from each other. Still more preferably, the library includes at least 48 samples and at least 90% of said samples included in the library are different from each other.

The substrate can be a structure having a rigid or semi-rigid surface on which or into which the library of samples can be formed, mounted, deposited or otherwise positioned. The substrate can be of any suitable material, and preferably includes materials that are inert with respect to the polymer samples of interest, or otherwise will not materially affect the mechanical or physical characteristics of one sample in an array relative to another. Exemplary polymeric materials that can be suitable as a substrate material in particular applications include polyimides such as Kapton™., polypropylene, polytetrafluoroethylene (PTFE) and/or polyether etherketone (PEEK), among others. The substrate material is also preferably selected for suitability in connection with known fabrication techniques. Metal or ceramic (e.g., stainless steel, silicon, including polycrystalline silicon, single-crystal silicon, sputtered silicon, and silica ($SiO_2$) in any of its forms (quartz, glass, etc.)) are also preferred substrate materials. Other known materials (e.g., silicon nitride, silicon carbide, metal oxides (e.g., alumina), mixed metal oxides, metal halides (e.g., magnesium chloride), minerals, zeolites, and ceramics) may also be suitable for a substrate material in some applications. Another suitable substrate is a silicon wafer that has been patterned to define a predetermined configuration on which the sample or samples are deposited (e.g., suspended deflectable arms). As to form, the sample containers formed in, at or on a substrate can be preferably, but are not necessarily, arranged in a substantially flat, substantially planar surface of the substrate. The sample containers can be formed in a surface of the substrate as dimples, spots, wells, raised regions, trenches, or the like. Non-conventional substrate-based sample containers, such as relatively flat surfaces having surface-modified regions (e.g., selectively wettable regions) can also be employed. The overall size and/or shape of the substrate is not limiting to the invention. The size and shape can be chosen, however, to be compatible with commercial availability, existing fabrication techniques, and/or with known or later-developed automation techniques, including automated sampling and automated substrate-handling devices. The substrate is also preferably sized to be portable by humans. The substrate can be thermally insulated, particularly for high-temperature and/or low-temperature applications.

In certain preferred embodiments, the substrate is formed to securely maintain contact with a plurality of samples. According to various methodologies it may be desirable to place forces on samples while the samples remain secured to the substrate. Forces may be applied to the samples by one or more members separate from the substrate or the substrate may apply the forces.

Non-Polymer Sample Materials

Some aspects of the invention can have applications involving non-polymer samples, non-polymer elements or compounds can include organic or inorganic pigments, carbon powders (e.g., carbon black), metals, metal compounds, metal oxides, metal salts, metal colloids, metal ligands, etc., without particular limitation. Other materials, which may be characterized according to the present invention include, without limitation, ceramic materials, semiconducting and conducting materials, metal and composites. Still other materials for which the present application finds untility are discussed elsewhere herein.

Sample Handling

Handling of sample materials may be accomplished with a plurality of steps which include withdrawing a sample from a sample container and delivering at least a portion of the withdrawn sample to a substrate. Handling may also include additional steps, particularly and preferably, sample preparation steps. In one approach, only one sample is withdrawn into a suitable liquid or solid dispensing device and only one sample resides in the probe at one time. In other embodiments, multiple samples may be drawn. In still other embodiments, multiple dispensers may be used in parallel.

In the general case, handling can be effected manually, in a semi-automatic manner or in an automatic manner. A sample can be withdrawn from a sample container manually, for example, with a pipette or with a syringe-type manual probe, and then manually delivered to a loading port or an injection port of a characterization system. In a semi-automatic protocol, some aspect of the protocol is effected automatically (e.g., delivery), but some other aspect requires manual intervention (e.g., withdrawal of samples from a process control line). Preferably, however, the sample(s) are withdrawn from a sample container and delivered to the characterization system in a fully automated manner—for example, with an auto-sampler.

In one embodiment, handling may be done using a microprocessor controlling an automated system (e.g., a robot arm). Preferably, the microprocessor is user-programmable to accommodate libraries of samples having varying arrangements of samples (e.g., square arrays with "n-rows" by "n-columns", rectangular arrays with "n-rows" by "m-columns", round arrays, triangular arrays with "r-" by "r-" by "r-" equilateral sides, triangular arrays with "r-base" by "s-" by "s-" isosceles sides, etc., where n, m, r, and s are integers).

Analytical Systems and Methods

According to the present invention, one or more systems, methods or both are used to determine the mechanical properties of a plurality of sample materials. Though manual or semi-automated systems and methods are possible, preferably an automated system or method is employed. A variety of robotic or automatic systems are available for automatically or programmably providing predetermined motions for handling, contacting, dispensing, or otherwise manipulating materials in solid, fluid liquid or gas form according to a predetermined protocol. Such systems may be adapted or augmented to include a variety of hardware, software or both to assist the systems in determining mechanical properties of materials. Hardware and software for augmenting the robotic systems may include, but are not limited to, sensors, transducers, data acquisition and manipulation hardware, data acquisition and manipulation software and the like. Exemplary robotic systems are commercially available from CAVRO Scientific Instruments (e.g., Model NO. RSP9652) or BioDot (Microdrop Model 3000).

Figure 2:
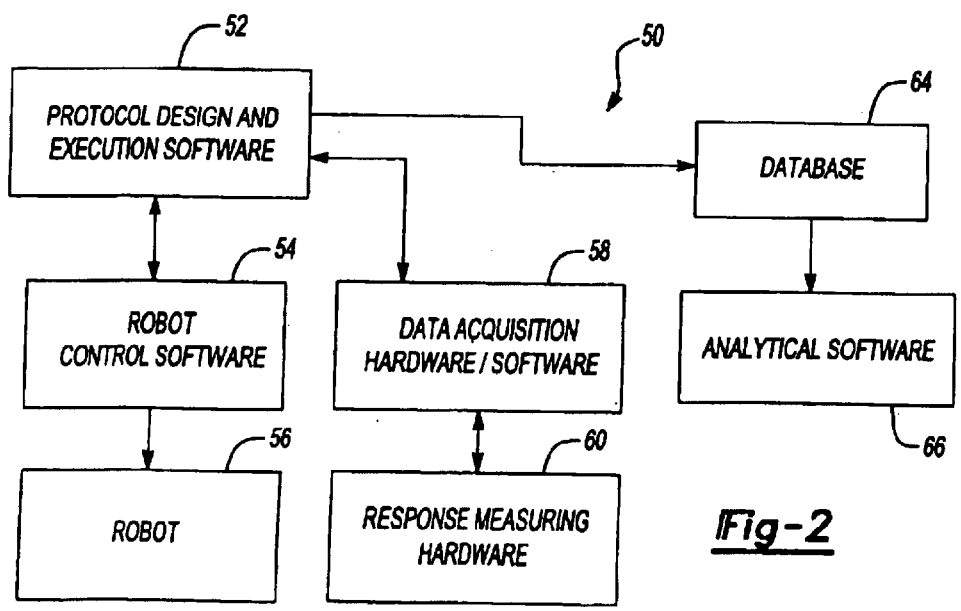
FIG. 2 is a block diagram of a potential platform system for executing methods and for operating systems of the present invention.

Referring to FIG. 2, there is a flow schematic diagram of an exemplary automated system 50 for rapid determination of mechanical properties of several samples of material. Generally, the system 50 includes a suitable protocol design and execution software 52 that can be programmed with information such as synthesis, composition, location information or other information related to a library of materials positioned with respect to a substrate. The protocol design and execution software is typically in communication with robot control software 54 for controlling a robot 56 or other automated apparatus or system. The protocol design and execution software 52 is also in communication with data acquisition hardware/software 58 for collecting data from response measuring hardware 60. Preferably, the robot control software 54 commands the robot 56 to apply stimuli to sample materials to evoke a response from the materials. At substantially the same time, the response measuring hardware 60 (e.g., sensors, transducers, load cells and the like) monitors the responses of the materials, the stimuli being applied to the materials or both and provides data on the responses to the data acquisition hardware/software 58. Thereafter, the robot control software 54, the data acquisition hardware/software 58 or both transmit data to the protocol design and execution software 52 such that the sample materials or information about the sample materials may be matched with their responses to the applied stimuli and transmitted at data to a database 64. Once the data is collected in the database, analytical software 66 may be used to analyze the data, and more specifically, to determine mechanical properties of the sample materials, or the data may be analyzed manually.

In a preferred embodiment, the system is driven by suitable software, such as LIBRARY STUDIO®), by Symyx Technologies, Inc. (Santa Clara, Calif.); IMPRESSIONIST®, by Symyx Technologies, Inc. (Santa Clara, Calif.); EPOCH™, by Symyx Technologies, Inc. (Santa Clara, Calif.) or a combination thereof. Moreover, data collected or produced by the system may be viewed using other suitable software such as POLYVIEW™, by Symyx Technologies, Inc. (Santa Clara, Calif.). The skilled artisan will appreciate that the above-listed software can be adapted for use in the present invention, taking into account the disclosures set forth in commonly-owned and copending U.S. patent application Ser. No. 09/174,856 filed on Oct. 19, 1998, U.S. patent application Ser. No. 09/305,830 filed on May 5, 1999 and WO 00/67086, U.S. application Ser. No. 09/420,334 filed on Oct. 18, 1999, U.S. application Ser. No. 09/550,549 filed on Apr. 14, 2000, each of which is hereby incorporated by reference. Additionally, the system may also use a database system developed by Symyx Technologies, Inc. to store and retrieve data with the overlays such as those disclosed in commonly-owned and copending U.S. patent application Ser. No. 09/755,623 filed on Jan. 5, 2001, which is hereby incorporated by reference for all purposes. The software preferably provides graphical user interfaces to permit users to design libraries of materials by permitting the input of data concerning the precise location on a substrate of a material (i.e., the address of the material). Upon entry, the software will execute commands to control movement of the robot, for controlling activity at such individual address.

In FIG. 6, there is illustrated one exemplary automated robot or apparatus 56 that may be operated using the system 50 of FIG. 2. As shown in FIG. 6, the apparatus 56 includes a pair of robot arms 70 appropriate for manipulating sample materials 72 located upon substrates 74.

Many of such aspects of the invention can be directly translated for use with parallel, serial or serial-parallel protocols. In a most preferred embodiment, for example, a rapid serial force system and protocols for that system can be used for characterization of materials with very high sample throughput.

Mechanical Strength Analysis

The system and method of the present invention may determine mechanical strength or collect information related to the mechanical strength of individual members of one or more libraries of materials. As used herein, a determination of strength of a material should be construed as including determinations of strength itself and determinations of responses such as deformations of sample materials that are related to strength. According to one embodiment a stimulus such as a force (e.g., stress) is applied, either manually or automatically, to each member of the array of materials using a probe, an actuator or other device. As the stimulus is applied the response of the materials due to the stimulus is monitored using a transducer (e.g., a sensor). Thereafter, one or more strengths of each of the materials in the array are determined based upon the response exhibited by the materials and based upon predetermined factors such as the geometry of the material samples, the geometry or configuration of the probe that provides the stimulation and the like.

Generally, the stimulus will be a force that is applied to the materials. The force applied to the material may be any suitable force such as tensile, compressive, torsional, shear, expansive or a combination thereof. The forces may be continuous, variable, intermittent, vibratory, repetitive or otherwise. The forces may be applied, recorded or both as a function of time. The forces may be applied with one of the robots or automated systems previously discussed or by another suitable robot or machine. The force may be applied by direct contact of a sample with a solid, such as with a probe, or through the direction of a fluid toward or away from the sample. For example, sample materials may be placed in a pressurized liquid or gas to compress the materials so that compressive strength of the material may be determined. They may be placed in a sealed chamber and a vacuum or other negative pressure applied. Alternatively, sample materials may be physically attached to two or more members wherein at least one of the members is moveable toward or away from another member to respectively exert compressive or tensile force upon the materials.

In other alternative embodiments, each member of the array of materials may be attached to one or more substrates and a robot or other automated system may exert forces upon the materials while the materials remain attached to the substrate. In that case, the transducer (e.g., a load cell) may be attached to the substrate such that the force applied to each sample material may be measured as it is applied to the entire substrate. Alternatively or additionally, a transducer (e.g., a load cell or displacement measurement device) may be attached to one or more probes and the probe[s] may measure the force applied to each sample on the substrate or the response of each sample on the substrate. Moreover, each of the material samples may be attached to or supported by its own portion (e.g., a chip, block or the like) of the substrate and the substrate may include a transducer corresponding to each portion of the substrate for individually measuring force applied to material samples or for individually measuring the response of the material samples.

The forces may be predetermined or may be measured or monitored as they are applied. The forces may be applied using one or more than one member or device for exerting one or more than one force on each sample. Alternatively, one member or device may exert one or more forces on a plurality of samples. The forces may be applied by moving sample materials relative to a probe, by moving a probe relative to the sample materials or a combination thereof. Moreover, individual material samples or groups of samples may be sequentially transported in vials, on other substrates or alone to a location adjacent the probe, the actuator, the transducer or the like for performing measurements on the material samples.

Other suitable forces may be employed as well, including but not limited to those obtainable electrically, electromagnetically, piezoelectrically, magnetically, thermally or the like.

A variety of transducers such as sensors, load cells and the like may be used within the systems for monitoring and/or measuring the forces being applied to the materials, the strains of the materials or both. Load cells may be used for monitoring forces being applied to materials. The loads cell may be attached to or contacting the robots, automated systems, substrates, materials being tested or a combination thereof. A multitude of sensors such as resistive, optical, visual, x-ray diffractive or other suitable sensors may be used to monitor strain or deformation of materials resulting from forces exerted on those materials. Alternatively, sensors having members that moveably contact the materials, substrates, automated systems or combinations thereof to assist in monitoring strains of materials may be used. One or more transducers or sensors may be used to monitor each sample. Alternatively, sensors may be used to monitor a plurality of samples. Thus, depending upon the transducer used, a strain of a material may be measured as the strain is induced by a predetermined force, a force may be measured as a predetermined strain is induced in the sample or a force and a strain of a sample may be measured together for each sample material.

The strains of the materials that are measured may involve compression, elongation, deflection, torsion, expansion or shearing of the materials. The strains of the materials may be elastic, plastic or may deform the materials to failure. Additionally, the materials may be deformed in one, or more than one direction.

In addition to measuring strains of the sample materials, other responses of sample materials may be measured as well. As an example, a sample material of an original predetermined configuration may be subjected to a force that causes a predetermined deformation or strain of the sample material. Once the predetermined deformation or strain has been achieved, the force needed to cause the deformation or strain and/or the force exhibited by the sample material in an effort to return to its original predetermined configuration may be measured and/or monitored. Then, the monitored or measured forces may be correlated to the deformation or strain of the sample material and to the dimensions of the original predetermined configuration of the sample material for determining strength of the sample material.

As an example, strengths of the materials may generally be determined by relating the strains of the materials to the force per unit area applied to the materials. The system and method may be designed to determine elastic strengths, yield strengths, ultimate strengths, fracture strengths, fatigue strengths, the strengths of a material for predetermined forces applied to the materials or other suitable strengths. Moduli such as flexural, tensile, compressive, torsional, elastic or other Moduli may be measured, calculated, or otherwise used to assist in determining strengths of materials. In a preferred embodiment, the materials may be formed to have a portion with a smaller predetermined cross-sectional area that is expected to fail when force is applied to the material. Then, the cross-sectional area and the force used to cause failure can be used to determine the strength of the material.

Figure 3:
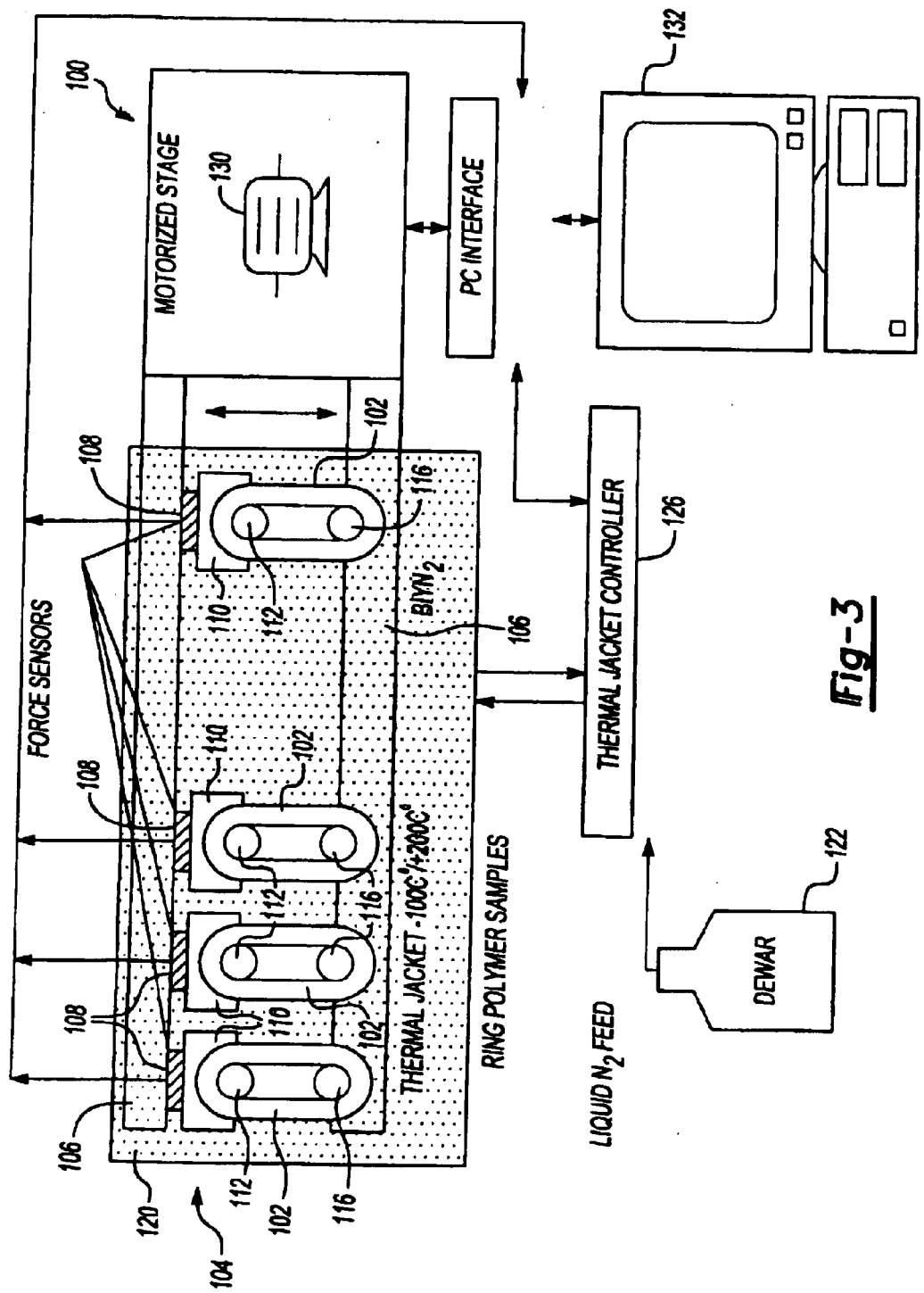
FIG. 3 is a schematic of a system for assisting in determining mechanical properties of materials in accordance with the present invention.

Referring to FIG. 3, there is illustrated one embodiment of a system 100 for measuring mechanical strength of a library of sample materials 102. The system 100 includes a substrate 104 having a pair of opposing jaw members 106. One of the jaw members 106 is associated with a plurality of force sensors 108, which may be attached to one or more suitable sample mounting block 110. Each block 110 including a pin or other like device for engaging a test specimen 112. The other opposed member 106 includes several pins 116 corresponding to and opposing the pins 112 of the blocks 110. In the present embodiment, the sample materials 102 are preferably provided in a solid state. For example as shown, they are configured as loops 102 and are looped about one attachment member 112 (e.g. a pin) attached to the one of the opposing members 106 and another opposing attachment member (e.g. pin) 116 attached to the other opposing jaw 106. The loops 102 may range in size and thickness. For example, thicknesses of cross-sections of the loops 102 may range from 0.1 mm to 10 mm and more preferably from about 1 mm to about 3 mm. Moreover, the size of the loops (i.e., a distance defined as a circumference or outer perimeter of the loop) may range from about 10 mm to about 1000 mm and more preferably from about 50 mm to about 500 mm.

Optionally, as shown in FIG. 3, the system 100 further includes a suitable apparatus, such as a thermal jacket 120 for heating and cooling the materials 102. One preferred thermal jacket 120 includes passages (not shown) for receiving a heated or cooled fluid such as liquid nitrogen, water, steam or other suitable fluid from a fluid supply 122. The fluid from the fluid supply 122 may be pumped to the thermal jacket 120 with a pump (not shown) that is controlled by a controller 126.

In operation, the material samples 102 are loaded onto the pins 112, 116, the materials 102 are heated or cooled as desired (e.g., preferably between −100° C. and 200° C.) by the thermal jacket 120, and the opposing members 106 are moved toward or moved away from each other such that the pins 112, 116 place a force upon the materials 102. The amount of force being applied to each material 102 is being monitored by the force sensors 108. Preferably, the opposing jaws 114 are moved relative to each other using a suitable actuator, such as a motor 130 or otherwise. As can be seen one or more computerized systems 132 may be used to control the conditions for testing, such as the heating and cooling of the materials 102, the rate at which the opposing jaws 106 move relative to each other and the forces being applied to each of the materials 102.

Figure 4:
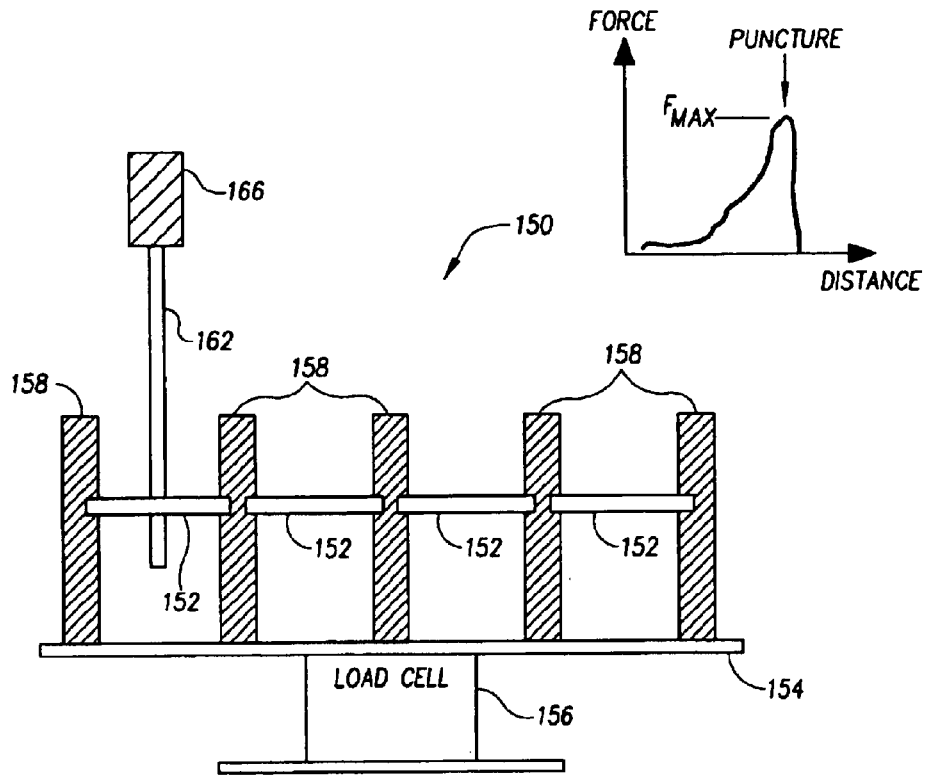
FIG. 4 is a schematic of a system for assisting in determining mechanical properties of materials in accordance with the present invention.

Referring to FIG. 4, there is illustrated another alternative system 150 for measuring strengths of sample materials 152. As shown, the system 150 includes a substrate 154 mounted atop at least one load cell 156. The substrate 154 includes a plurality of spaced apart support members 158. A plurality of sample materials 152 are attached to one or more of the support members 158. Preferably, each of the sample materials 152 is a sheet (e.g. a single layer or multi player film, a coated or uncoated substrate or foil, a woven or unwoven fabric, or the like). The sheet may be spanned and secured at the ends of each sample or about the periphery of each sample, such as by opposing support members 158. The system also includes a probe 162 for placing a force upon each of the materials 152. Preferably, the probe 162 is attached to a robot or other automated system (not shown) with a spring 166 for placing a force upon each of the sample materials 152 until the sample material 152 fails (e.g., rupture, rips, punctures, tears or otherwise). As the probe 162 applies a force (e.g. by pushing or pulling the sample) to the sample materials 152 the load cell 156 measures the amount of force being applied such that the failure strength (i.e., the amount of force or stress required to make the materials 152 fail) of each of the materials 152 may be determined. Advantageously, the spring 166 provides a cushion to the amount of force being applied by the probe 162 such that the force may be more accurately monitored. It may also be advantageous to provide more than one load cell to support and balance the substrate 154 such that forces applied to the materials 152 are measured rather than torques or moments. Shear may also be measured, for instance, by notching the sample and measuring growth of the notch in response to the probe force.

It will be appreciated that any of a number of additional stimuli may be introduced and the effects of which analyzed. For example, cyclical loading with a suitable motor can be employed for addressing fatigue strength of each sample. Additionally, various environmental conditions such as humidity, temperature, pressure and the like may be altered (e.g., raised or lowered) around the sample materials to vary tests of the sample materials.

Tack or Adhesive Measurements

The system and method of the present invention may also determine adhesive properties such as tack, shear and the like for each member of an array of materials. As used herein, the term adhesive and its conjugations should be construed as including adhesive strength and all of the properties or quantifications related to adhesion. According to one embodiment of the invention, a stimulus such as a force is applied to each of the materials with a member. The force is applied to oppose adhesive forces of the materials that try to maintain a connection with the member or a substrate to which the materials are adhesively secured. During application of the forces responses of the materials are monitored and the responses are used to determine the adhesiveness or tack of each of the materials.

Preferably, each member of the library of materials includes a surface that is flat, curved, contoured or is otherwise adapted for adhesively contacting a corresponding surface of a member (e.g., a probe). Thereafter, the member is moved at least partially away from the surface of the materials to apply a force in opposition to tack or adhesive forces of the materials. The force applied to the materials may be tensile, compressive, shear or a combination thereof. The force may be continuous, intermittent, vibratory, repetitive or otherwise. The force may be applied with one of the robots or automated systems previously discussed or by another suitable robot or machine. The forces may be predetermined or may be measured or monitored as they are applied. The forces may be applied using one or more than one member or device for exerting one or more than one force on each sample. Alternatively, one member or device may exert one or more forces on a plurality of samples.

Responses of the materials may include the tack or adhesive forces exhibited by the materials in response to forces provided by the members. The responses may also include the deformation of the materials in response to the forces provided by the members. Suitable sensors may be used to measure the deformation of the materials such as visual, optical, resistive, thermal or other sensors. One or more sensors may be used to monitor each sample. Alternatively, sensors may be used to monitor a plurality of samples.

Adhesiveness may be determined for example, by relating the deformation and/or the forces applied by the members to the adhesiveness of the materials. Adhesiveness properties may be determined using a variety of engineering equations to relate responses of the materials to the adhesive properties of the materials. As an example, a law such as Stephen's law of Tack may be used:

$$\text{Tack}=(\text{Area})(\text{Viscosity})(\text{Speed})/(\text{Distance})^3$$

wherein area refers to the contact area between a member and a material, viscosity is the viscosity of the material, speed is the rate at which the member is moved away from the material and distance is the distance from the contact surface of the member used for contacting the materials to the contact surface of another member (e.g. a substrate) to which the materials are contacted or attached.

Figure 5:
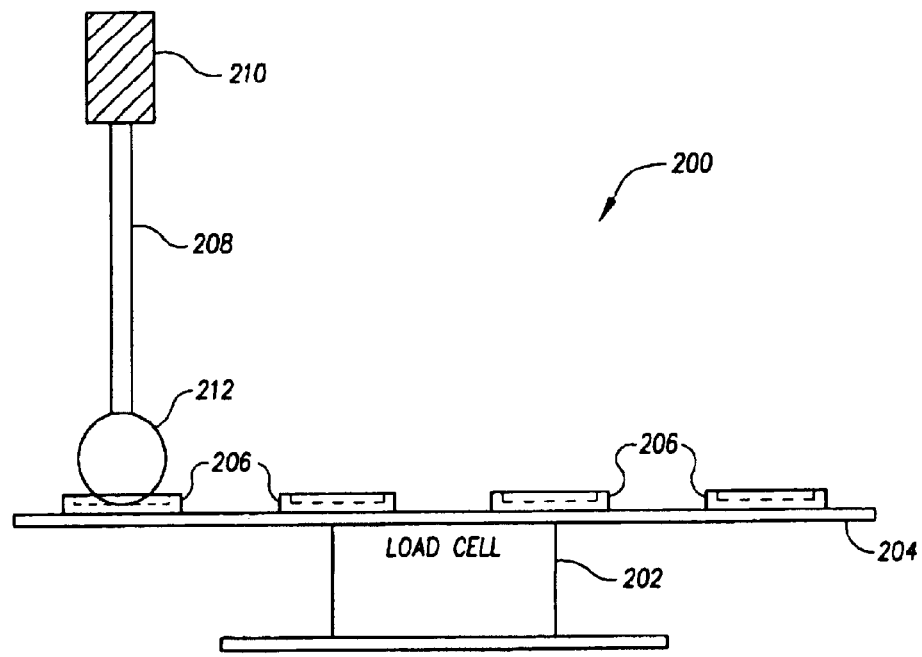
FIG. 5 is a schematic of a system for assisting in determining mechanical properties of materials in accordance with the present invention.

Referring to FIG. 5, there is illustrated a system 200 including a load cell 202 supporting a substrate 204, which, in turn is supporting a plurality of samples 206. An appropriate probe 208 is located adjacent the substrate 204 for applying forces to the samples 206. Preferably, the probe 208 includes a surface for contacting the samples 206 provided by a contacting portion 212 to allow the samples 206 to adhesively secure themselves to the probe 208. In one highly preferred embodiment, the contacting portion 212 may be a loop of flexible material wherein the pressure or force with which the loop contacts the samples 206 is dependent upon the flexure or stiffness of the loop, thus making the contacting force controllable. Thereafter, the probe 208 is moved away from the samples 206 to displace or strain the samples and/or to oppose adhesive forces of the samples 206. Preferably, the probe 208 includes a distance measuring device 210, such as an LVDT, non-contact sensors (e.g., inductive, capacitive or optical probes), for determining the distance that a contacting portion 212 of the probe 208 displaces at least a portion of the samples 206 for a given amount of force applied by the probe 208. In a preferred embodiment, the probe 208 could be moved by a robot or other automated system (not shown) to provide a force upon each of the samples 206 and the load cell 202 and the distance measuring device 210 could be in communication with the data acquisition hardware/software to collect data there from so that a tack or other adhesive measurement could be determined for each sample 206. It is also contemplated that the system 200 does not include a distance measuring device and that tack is determined at least for comparative purposes by the force required to move a probe away from the sample.

Figure 5A:
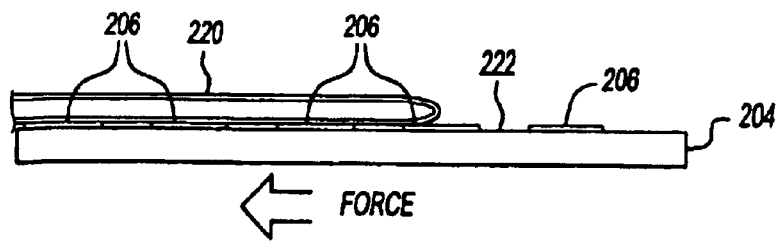
FIGS. 5(a)–5(c) are schematics of alternative systems for assisting in determining mechanical properties in accordance with the present invention.
Figure 5B:
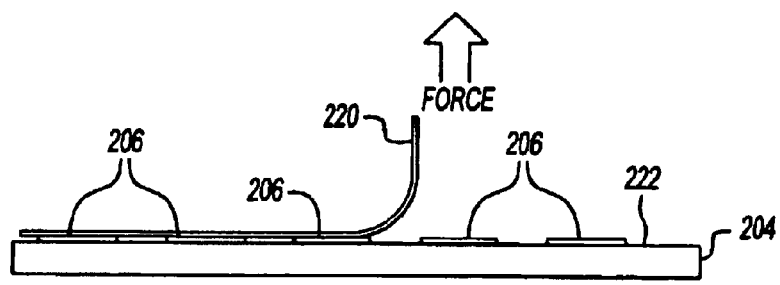
Figure 5C:
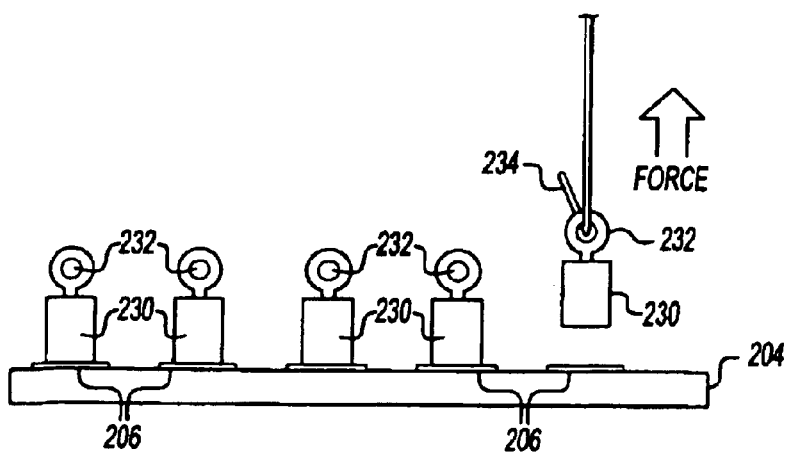

Referring to FIGS. 5(a)–5(c), there are illustrated alternative probes for providing alternative forces to the samples 206. In FIG. 5(a), a flexible probe 220 is used for peel testing a plurality of samples 206. The flexible probe 220 (e.g., a flexible sheet or tape) is adhesively secured to a plurality of samples 206 wherein the samples 206 are secured to a surface 222 of the substrate 204. According to one embodiment, a plurality of flexible probes 220 may be laid upon a plurality of rows of samples 206. Alternatively, a flexible sheet may be laid upon a plurality of samples and the sheet may be cut (e.g., with one or more razors mounted to a handle, a scalpel or the like) so that the probes 220 are adhered to individual rows of samples. Once in place, one or more probes 220 are pulled off of each sample 206 by a force applied to the probe 220. The probes 220 may be pulled off in any desired direction or at any desired angle. Alternatively the substrate 204 may be moved relative to the probes 220. In FIG. 5(a), the probe 220 is pulled of in a direction that is substantially parallel to a surface 222 of the substrate 204, to which the samples 206 are secured. In FIG. 5(b), the probe 220 is pulled off of the sample 206 by a force applied to the probe 220 in a direction substantially perpendicular to the surface 222 of the substrate 204. Preferably, the probes 220 are pulled off the samples 206 automatically by an automatic system (not shown) such as a robot arm and are pulled off in a predetermined direction, at a predetermined angle or both. Either, the probe 220, the automatic system or both may be fitted with one or more mechanisms to allow the automatic system to releasably secure itself to the probes 220. Exemplary releasable attachments may comprise a hook attached to the automated system and a loop formed in the probe 220 or other such mechanisms. It is also preferable for either the automatic system or the substrate 206 to include a force measuring device or sensor (not shown) such as a load cell or other sensor for determining the amount of force needed to remove the probes 220 from the samples 206.

In FIG. 5(c), several probes 230 are individually adhesively secured each to a different sample 206. The weight of the probes 230 by be predetermined to provide a desired contacting pressure and the probes 230 may be allowed to set upon the samples 206 for a predetermined amount of desired contacting time. In this manner, the degree of adhesiveness or tack of the samples may be determined for such contacting times and pressures which may be critical or not critical depending upon the desired application of the sample materials. Preferably, each of the members 230 includes a mechanism for removing the member 230 from the samples 206. For instance, each member 230 may include a loop 232 attached to it such that a hook 234, preferably attached to a robot or other automated system that can pull each member off of its respective sample 206 thereby providing a force to the sample 206. Again, either the automated system or the substrate 204 is preferably fitted with a force sensor to determine the force used to move or remove the probes 230 from the samples 206.

In certain circumstances, it may be desirable to obtain measurements of the adhesiveness of material samples in terms of shear strength (i.e., the resistance of an adhesive bond against forces acting along or parallel to the plane of the bond). In such circumstances, one or more members or probes such as chips, fabrics, dies or non-adhesive tapes may be placed such that a surface of the members contacts each of a set of material samples. Preferably, each of the members include a releasable attachment that can be engaged by an automatic system (e.g., a robot arm). Thereafter, the automatic system, which is preferably fitted with a force sensor can apply a force parallel to the plane of the surface of the members contacting the sample. As the force is applied, it can be measured and monitored using the sensor preferably as a graphed profile of force versus time. The force applied to the members may or may not remove the members from the material samples.

In any or all of the above embodiments adhesive properties may be quantified in terms of forces applied. Forces applied per unit surface area of sample or otherwise quantified.

In other alternative embodiments, it is contemplated that frictional forces may be applied to samples for testing material sample properties such as frictional responses, frictional coefficients, wear strength, frictional wear strength or the like. As used herein, the term frictional force means any force applied by contacting a surface of a member with a surface of a sample and urging the surface of the member to slide, translate or rotate at least partially along the surface of the sample. According to this definition, it is unnecessary for the surface of the member to slide along the surface of the sample, only that it be urged to do so. Of course, the surface of the member actually sliding along the surface of the sample is also included within the definition. Thus, both kinetic and static friction forces may be measured. In certain preferred embodiments, a surface of a probe is contacted with a surface of a sample and the probe surface is rotated relative to the sample surface. Advantageously, such rotational frictional forces can be applied at relatively rapid rates to several samples.

For certain preferred embodiments the frictional forces applied to the samples may be repetitive. As used herein, the term "repetitive frictional force" means a frictional force that is applied to a sample after application of a first or preceding frictional force to that sample. There is no requirement that a repetitive frictional force be the same as a force preceding it, although it is certainly contemplated that a repetitive frictional force may be the same as its preceding force. As an example of a repetitive frictional force, it is contemplated that an automated or manual system may slide a surface of a probe back and forth across a surface of a sample. As another example, a surface of a probe may be translated repetitively in a substantially singular direction across a sample.

Several different types of members may be employed for application of frictional forces to samples and the forces may be applied using a variety of techniques (e.g., manual, automatic or a combination thereof). Preferably, the forces are applied with an automated system (e.g., a robot arm) that moves a contact surface of a member such as a probe relative to the samples of a combinatorial library. The contact surface of the member or probe may be in a variety of configurations including pointed, contoured, flat, spherical, geometric or the like. Moreover, the probe may be configured in a variety of shapes and sizes depending upon the type, amount or the like of contact desired.

For exemplary purposes and referring to FIGS. 7(a)–7(c), there are illustrated three exemplary potential probes 250, 252, 254, which may be employed in the present invention. Each of the exemplary probes 250, 252, 254 are generally elongated and respectively include contacting surfaces 260, 262, 264. As shown, the contacting surface 260 of one probe 250 is at least partially spherical (e.g., hemispherical). The contacting surface 262 of another probe 262 is substantially conical. Moreover, the contacting surface 264 of still another probe 254 is geometric (i.e. includes two or more intersecting planar surfaces).

The samples for friction force testing may be any of those disclosed herein. In certain preferred instances, however, the samples are preferably formed from panel materials (e.g., fabrics, laminates, polymer films or the like). Moreover, the panel materials may be in a variety of configurations. For example, a single panel material may have a variety of additives (e.g., coatings or other materials) applied at discrete locations upon the single panel material such that the single panel material provides several different panel material samples. Alternatively, several separate panel material samples of the same panel material may be provided with different additives for differing the panel material samples. As another alternative, several separate panel material samples formed of at least slightly different panel materials may be provided as differing panel material samples.

It is contemplated that friction force testing may be applied to a variety of panel materials. As examples, panel materials may formed of paper, textiles, non-woven or woven materials, polymer (e.g., plastic or rubber) films, painted and unpainted substrates of wood, metal, building materials or the like, glass, leather or otherwise. It is further contemplated that additives may be applied to each of the materials and the additives may coat or otherwise treat the materials. As examples, additives may include hardeners, softeners, paints, chemicals, natural elements and components, protectants, lubricants, oils or the like.

Several of the different substrates mentioned herein and various other substrates as well may be suitable for supporting samples during frictional screening. Preferably, such substrates support material samples such that a large enough area of a surface of each of the samples is accessible to a probe for allowing a surface of the probe to be slid across the surface of the samples. For panel materials and samples formed therefrom, it is preferable that the substrates have the ability to maintain the surfaces of the samples relatively taut as they are contacted with a probe during testing (e.g., flexing less than 5 mm and more preferably 10 mm due to contact from the probe).

Figure 8:
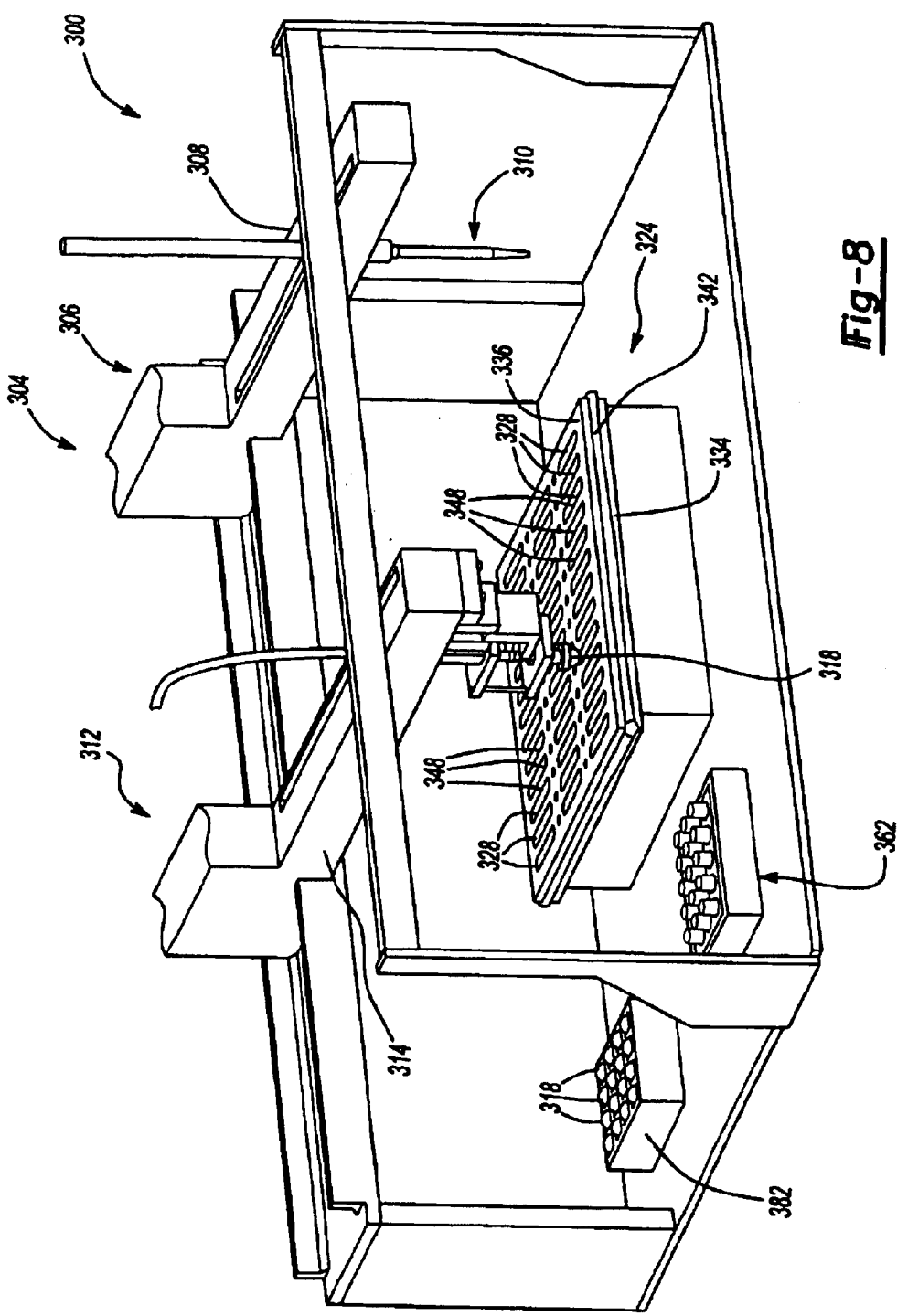
FIG. 8 is another exemplary automated apparatus or system for assisting in determining mechanical properties in accordance with the present invention.
Figure 9:
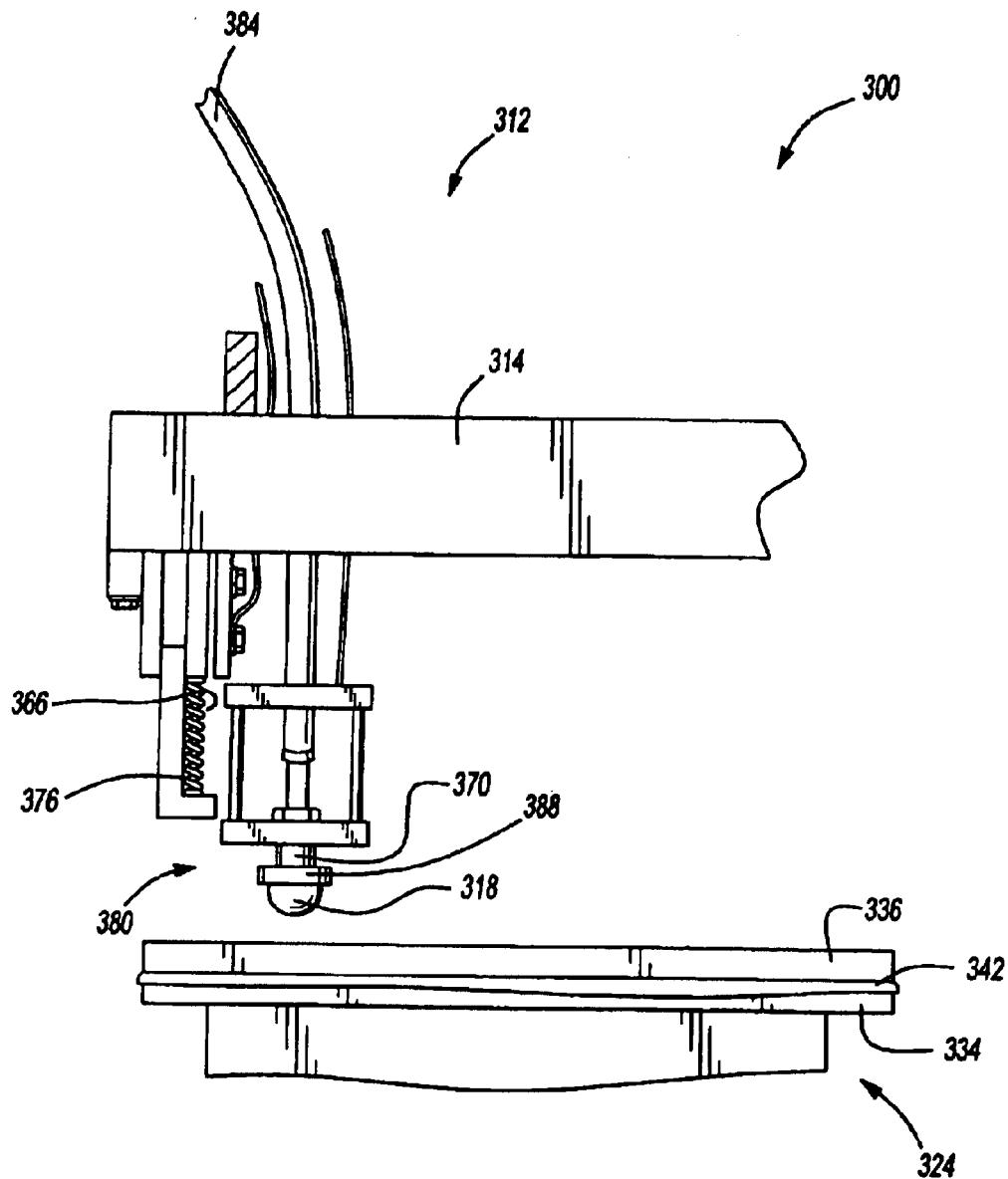
FIG. 9 is a side view of a portion of the exemplary apparatus or system of FIG. 8.

Referring to FIGS. 8 and 9, there is illustrated an exemplary system 300 for applying frictional forces to samples 302 for friction screening of the samples 302. The system 300 includes an x-y-z robot 304 with a dispensing sub-system 306 having a first robot arm 308 and a dispenser 310 (e.g., a syringe and plunger system) mounted thereon and a force application sub-system 312 having a second arm 314 supporting a probe 318. The system 300 also includes a substrate 324 for supporting a combinatorial library of material samples 328.

In the embodiment shown, the substrate 324 includes a base portion 334 and a clamp portion 336. The base portion 334 provides a surface 340 for supporting a panel material 342. The clamp portion 336 can preferably be removably fastened to the base portion 334. As shown, the clamp portion 336 includes a plurality of openings 348 (e.g., elongated slots).

For forming a combinatorial materials sample library, one or more panel materials 342 (e.g., fabrics, films or the like) are positioned between the clamp portion 336 and the base portion 334 of the substrate 324 such that discrete portions of the one or more panel materials 342 are accessible through the openings 348 of the clamp portion 336. In such an embodiment, it may be advantageous to used an adhesive between the clamp portion 336 and the base portion 334 to assist in securing the one or more samples 302 at least partially therebetween. In particular, it may be desirable to use adhesive surrounding the openings 348 and/or samples 328.

For forming samples the robot arm 308 of the dispensing sub-system 306 is employed for dispensing aliquots of liquid materials or additives through the openings 348 and onto the discrete portions of the panel material 342 thereby forming the discrete portions into the combinatorial library of panel material samples 302. As discussed previously, it is preferable for the samples of a combinatorial library to be differed with respect to each other and it is contemplated that such differing of samples may be achieved by employing any of the previously discussed dispensing protocols or other protocols for dispensing the various additives discussed herein upon the panel material 342.

For the specific substrate 324 of FIGS. 8 and 9, it is preferred that the aliquots of liquid additives be dispensed relatively continuously along the elongation of the openings 348 to the discrete regions of the fabric material 350. For achieving such continuity, the dispensing sub-system 306 (e.g., the dispenser 310) preferably has the ability to dispense liquids at a substantially continuous rate as the dispenser 310 is translated via the robot arm 308 at a substantially continuous rate relative to the elongation of the openings 348. In the particular embodiment shown, a combinatorial library 362 of different coating sample liquids is provided for application to the discrete regions to form the samples.

Once formed, the library of panel material samples 302 is screened or otherwise tested for a material property, which, in the embodiment shown, is a friction response. For screening the friction response of the material samples 302, the robot arm 314 of the force application sub-system 312 preferably contacts the probe 318 with one of the samples 302 followed by sliding the probe 318 across the sample 302 while simultaneously measuring the frictional resistance of the sample 302 against the sliding. Thereafter, the force application sub-system 312 serially screens each of the samples 302 of the library in substantially the same manner.

For measuring the friction response of the samples 302, it is contemplated that a variety of transducers may be employed. In the embodiment shown, the force application sub-system 312 preferably maintains a relatively continuous known (e.g., predetermined or measurable) normal force urging contact between the probe 318 and the samples 302 as the probe 318 is slid across the sample 302. During such sliding, a load sensor 370, which is part of the force application sub-system 312 measures the amount of frictional force resisting movement of the probe 318 across the sample 302.

Advantageously and referring again to FIGS. 8 and 9, the system 300 includes a spring sub-system 366 for lowering any fluctuation in normal force that may be experienced by a more rigid system. As shown, a spring 376 is mounted on the robot arm 314 of the force application sub-system 312 such that the spring 376 can assist in lowering fluctuations in force (i.e., normal force) applied by the probe 318 as the probe 318 is slid across the samples 302. As shall be appreciated, the spring 376 tends to absorb and normalize the force applied by the probe 318 when contours of the samples 302 cause the probe 318 to move or fluctuate relative to the robot arm 314 or in directions skew to the intended direction of motion (e.g., the direction of sliding).

In a highly preferred embodiment, a force feedback network may be provided. Preferably, the force feedback network includes a force generator (e.g., an automated or robotic system), a transducer for measuring the force applied (e.g., a load sensor) and a control network (e.g., appropriate circuitry). In such an embodiment, the transducer preferably provides the control network with data regarding the amount of force being applied to a sample. In turn, the control network preferably provides a signal to the force generator commanding the force generator to lessen or increase the amount of force being generated such that the force generated is maintained at a desired substantially continuous value (e.g., a desired normal force).

In certain instances, it may be desirable to calculate a coefficient of friction for the samples. In particular, the coefficient of friction ($\mu$) may be calculated according to the equation:

$$\mu = F_f/F_N$$

wherein $F_f$ is the frictional force and $F_N$ is the normal force. Determination of the coefficient of friction ($\mu$) may be particularly advantageous when the frictional force ($F_f$) and the normal force ($F_N$) undergo fluctuations (e.g., fluctuations that are not fully or adequately accounted for by the spring sub-system 312) with respect to time as a probe is slid across a sample. In such an embodiment, an additional load sensor may be used to monitor the normal force ($F_N$) with respect to time and the coefficient of friction ($\mu$) may be determined with respect to time. In turn, a meaningful comparison can be made between the coefficients of friction of the library of samples.

In between measurements of samples, especially when the samples have a tendency to leave residue upon a probe, the probe may be cleaned or a portion (e.g., a contacting portion) of the probe may be replaced to assure accurate readings. Probes may be cleaned between testing of samples. For examples, the probes may be immersed in a cleaning solution, the probes may be exposed to a cleaning surface (e.g., a buffing wheel, cleaning pad or the like) or other techniques may be used. Alternatively, portions of probes or entire probes may be replaced between testing of samples. For instance, disposable probe tips such as balls, members or the like may be releasably attached to a probe (e.g., by suction, magnet or otherwise) such that the tips may be quickly attached and released from a probe, robot arm or both between testing of samples. As another example, and particularly for peel testing, flexible non-adhesive tape-like probes may be provided and replaced with a system of rollers, pulleys, cams or the like. To assure the cleanliness of the probe, a tack or adhesive measurement may be performed on a clean non-tacky, non-adhesive surface and, preferably, there is no adhesiveness measured for the clean surface thereby assuring that the probe has been properly cleaned, however, the presence of adhesiveness can indicate that the probe needs to be cleaned further or cleaned another way.

In the exemplary system 300 of FIGS. 1 and 2 a vacuum sub-system 380 is included for replacing probes 318 from a probe rack 382. The vacuum sub-system 380 includes a vacuum pressure source 384 (e.g., a tube) in fluid communication with a probe receiver 388 such that the probe receiver 388 can receive the probe 318 and vacuum pressure may be employed to at least temporarily secure the probe 318 to the receiver 388. In the embodiment shown, the probes 318 are spheres, or balls and the probe receiver 388 includes an at least partially spherical or otherwise mating cavity. Preferably the spheres are formed of rubber such as NEOPRENE®, which is commercially available for DuPont Corporation, although other materials (e.g., glass, metal or the like) may be used as well.

While the probes of FIGS. 1 and 2 are shown as spheres, it is contemplated that probes may be formed in a variety of shapes and configurations according to the present invention as previously discussed. In the same vane, it is also contemplated that a variety of configurations of probe receivers may be formed to accommodate the variety of probes.

In operation, the vacuum source 384 applies vacuum pressure to the probe receiver 388 and the robot arm 314 of the force application sub-system 312 moves the probe receiver 388 such that one of the probes 318 in the probe rack 382 is at least temporarily secured in the cavity of the probe receiver 388. Thereafter, the probe 318 is slid across one or more samples 302 as previously described followed by removal of vacuum pressure to release the probe 318 such that another probe 318 may be retrieved from the rack 382. As should be appreciated, it is preferable for the vacuum source 384 to apply enough force to the probe 318 such that the probe 318 does not rotate during screening of (e.g, application of frictional force) the library of samples 302. Alternatively, the probes 318, the receiver 388 or both may be fitted with a mechanical portion (e.g., members and/or cavities) for preventing such rotation. It should also be appreciated that, once a probe 318 has been employed for screening it may be cleaned or disposed of.

It will be appreciated that any number of additional stimuli may be introduced and the effects of which analyzed. For example, various environmental conditions such as humidity, temperature, pressure and the like may be altered (e.g., raised or lowered) surrounding the sample materials to vary tests of the sample materials.

Sample-Throughput

For methods directed to characterizing a plurality of samples, a property of each of the samples or of one or more components thereof is detected—serially or in a parallel, serial-parallel or hybrid parallel-serial manner—at an average sample throughput of not more than about 10 minutes per sample. As used in connection herewith, the term "average sample throughput" refers to the sample-number normalized total (cumulative) period of time required to detect a property of two or more samples with a characterization system. The total, cumulative time period is delineated from the initiation of the characterization process for the first sample, to the detection of a property of the last sample or of a component thereof, and includes any intervening between-sample pauses in the process. The sample throughput is more preferably not more than about 8 minutes per sample, even more preferably not more than about 4 minutes per sample and still more preferably not more than about 2 minutes per sample. Depending on the quality resolution of the characterizing information required, the average sample throughput can be not more than about 1 minute per sample, and if desired, not more than about 30 seconds per sample, not more than about 20 seconds per sample or not more than about 10 seconds per sample, and in some applications, not more than about 5 seconds per sample and not more than about 1 second per sample. Sample-throughput values of less than 4 minutes, less than 2 minutes, less than 1 minute, less than 30 seconds, less than 20 seconds and less than 10 seconds are demonstrated in the examples. The average sample-throughput preferably ranges from about 10 minutes per sample to about 10 seconds per sample, more preferably from about 8 minutes per sample to about 10 seconds per sample, even more preferably from about 4 minutes per sample to about 10 seconds per sample and, in some applications, most preferably from about 2 minutes per sample to about 10 seconds per sample.

A sample-throughput of 10 minutes per sample or less is important for a number of reasons. Systems that detect a property of a sample or of a component thereof at the aforementioned sample throughput rates can be employed effectively in a combinatorial research program. From a completely practical point of view, the characterization rates are also roughly commensurate with reasonably-scaled polymer sample library synthesis rates. It is generally desirable that combinatorial screening systems, such as the polymer characterization protocols disclosed herein, operate with roughly the same sample throughput as combinatorial synthesis protocols—to prevent a backlog of uncharacterized polymerization product samples. Hence, because moderate scale polymer-synthesis systems, such as the Discovery Tools™ PPR-48™ (Symyx Technologies, Santa Clara Calif.), can readily prepare polymer libraries with a sample-throughput of about 100 polymer samples per day, a screening throughput of about 10 minutes per sample or faster is desirable. Higher throughput synthesis systems demand higher characterization throughputs. The preferred higher throughput values are also important with respect to process control applications, to provide near-real time control data.

Additionally, as shown in connection with the examples provided herein, the characterization of polymer samples at such throughputs can offer sufficiently rigorous quality of data, to be useful for scientifically meaningful exploration of the material compositional and/or reaction conditions research space.

Hence, the average sample-throughput can range, in preferred cases, from about 10 minutes per sample to about 8 minutes per sample, from about 8 minutes per sample to about 2 minutes per sample, from about 2 minutes per sample to about 1 minute per sample, from about 1 minute per sample to about 30 seconds per sample and from about 1 minute per sample to about 10 seconds per sample, with preferences depending on the quality of resolution required in a particular case. For example, in some research strategies, the very high sample throughputs can be effectively employed to efficiently screen a polymer sample or component thereof having a particularly desired property (e.g., such as weight-average molecular weight). In short, the search can be accelerated for the particular property of research interest.

Calibration Methods and Standards

As desired the systems and methods of the present invention may optionally employ a calibration procedure. By way of example, a calibration standard is provided having a number of subcomponents that differ with respect to strength of a material. Such subcomponents are typically referred to as "known standards" or, simply, "standards" that are well characterized with respect to the calibrating property of interest. They are analyzed by the measuring apparatus of the present invention and the apparatus is adjusted as desired.

The accuracy and precision of the determination of material properties can vary depending on the type of measurement being conducted, the purpose of the measurements and the like. According to one embodiment the response, the stimulus or both applied to each of the material samples of the samples may be ranked or indexed and the ranked or indexed properties may be compared with each other. In such a case, accuracy and precision with regard to determining exact values of the properties of the sample materials may not be as important as assuring that the tests are performed consistently upon samples that are compared to each other since the object of the testing may be to determine which materials perform best rather than determining exact material properties. In other cases, such as when the stimuli and responses of the sample materials will be used to compare the sample materials to known properties of known materials, it may be more important to determine values for sample material properties such as Young's Modulus, shear modulus, tensile strength tack and the like that are closer to the absolute values of those properties for the sample materials to allow useful comparison's. The skilled artisan will recognize that the methods and apparatuses discussed above can be configured to be more or less accurate depending upon the equipment used and that the choice of equipment can depend on constraints such as monetary constraint and upon the amount of accuracy needed for a particular purpose.

Accuracy and precision for measurement of sample materials especially the deformation or displacement of the materials may also depend upon the nature of the samples being tested. Inherently, the instrumentation and testing equipment such as probes, robotic arms and substrates experience various amounts of deformation or strain as they apply a force to a sample material and, depending of the accuracy need or desired, that deformation or strain may need to be accounted for. Typically, softer materials such as gels, elastomers and the like tend to deform to a substantially greater degree than the instrumentation and testing equipment such that the deformation or strain of the latter may be inconsequential. However, more rigid sample materials such as plastics and the like can deform much less than the instrumentation and testing equipment. Therefore, for testing relatively rigid sample materials, it may be desirable to use rigid equipment for providing force to a sample or it may be desirable to measure the deformation of the sample with equipment that is separate from the equipment providing the force to the samples. Alternatively, it may be desirable to use a transducer mounted to a probe or other instrumentation for measuring total deformation of the testing equipment and the samples coupled with determination of the deformation of the testing equipment such that the deformation of the testing equipment may be subtracted from the total deformation to determine the deformation of the sample materials.

As an example, methods of the present invention may be performed using a probe mounted to an arm of an XYZ liquid handling robot. The arm carrying the probe, if supported only at one end, may flex or bend about the pivot point where the arm is supported. If the arm is supported at both ends, it may still bow in the middle when a force is applied to it. Thus is may be desirable to monitor the displacement of the probe relative to the arm using an additional sensor to precisely measure the displacement of the probe relative to the sample. Alternatively the deformation of the probe relative to the arm may be calculated for a variety of forces to determine a relationship between force and deformation of the probe. Such relationship may be plotted as a force-distance curve of the arm, supporting member, etc. Then, when a force is generated upon the sample, the corresponding deformation of the probe can be calculated and subtracted from the total deformation of the probe and the sample, to give the sample deformation.

As another example, a transducer or sensor may be used that is substantially unaffected by the strain or deformation of the equipment (e.g., the probe or robotic arm) being used to make measurements of sample materials. One example of such a sensor is a Linear Variable Displacement Transducer (LVDT), which may be assembled to the end of a probe or other equipment. Typically the LVDT will include a first portion that can be located in a stationary position relative to a substrate upon which one or more sample material are attached. Additionally, the LVDT may include a second portion that can be located in a stationary position relative to a surface (e.g., of a probe) that contacts the material samples for causing displacement of the samples. Thereafter, the LVDT only senses the movement of its first portion relative to its second portion wherein such movement is a direct measurement of the deformation or strain of a material sample since each of the first and second portions of the LVDT can only move relative to each other as much as the material sample deforms to allow movement between the surface to which the second portion is attached and the substrate to which the first portion is attached. In one example, the LVDT is a coil assembly with a push rod that can be rigidly attached to a probe directly adjacent to a surface of the probe that is configured for contacting samples. Thereafter, for testing material samples, the push rod contacts a substrate supporting material samples as the probe contacts the samples. As the probe is pushed against the sample, the LVDT rod is stationary relative to the substrate, but is moved into the coil assembly a distance that directly corresponds to the displacement of the surface of the probe, which in turn, corresponds to the deformation of each sample regardless of the deformation of the probe, robot or both.

Preparation of an Array of Fabric Samples

Fabric samples may be woven or unwoven, coated or uncoated, or aggregated with a suitable binder or not. The present invention is not limited to any particular type of fabric material and may include a woven material (e.g., batiste, chiffon, net, voile, organza, georgette, challis, chambray, charmeuse, crepe, dotted swiss, handkerchief linen, satin, eyelet, lace, velvet, taffeta, metallic, gauze, jacquard, gingham, percale, seersucker, broadcloth, brocade, linen, pique, shantung, chintz, velveteen, polyester blend acrylic, fleece, gabardine, denim, twill, corduroy, terry, velour, canvas, duck, percale, tergal, flannel, lame, tricotine, etc.), a non-woven material (e.g., felt, fusibles, interfacing, etc.), a knit material (e.g., atlas, jersey, pointelle, raschel, mesh, panne velvet, tricot, rib knit, double knit, interlock, intarsia, etc.), a pile material (e.g., chenille, chinchilla, faux fur, frieze, grospoint, tubular, etc.), a blend material (e.g., cotton/silk blend, cotton/wool blend, etc.), a composite material (e.g., laminated, etc.), or a combination thereof. The fabric materials can be natural (e.g., cotton, silk, linen, wool, hemp, ramie, jute, etc.), synthetic (e.g., acetate, acrylic, lastex, nylon, polyester, rayon, etc.), or combination thereof. They can also be acrylic coated, airo finished, bleached, resin treated, sanded, scented, sheared, silver coated, wax coated, stonewashed, bonded, enzyme washed, flocked, glazed, mercerized, milled/fulled, and subject to other textile treatments for color, texture, bacterial resistant, soil resistant, oil repellent, flame resistant, pill resistant water resistant, mildew resistant, water repellant, wrinkle resistant, or ultra violet resistant, etc. Standards (such as calibration standards) or blanks may be employed in the array for known scientific purposes. In this regard, the present invention is particularly attractive for the screening of effects of variations of textile treatments and/or additives (e.g., surfactants, fillers, reinforcements, flame retardants, colorants, environmental protectants, other performance modifiers, control agents, plasticizers, cosolvents, accelerators, etc.) upon the fabric handle of a fabric material.

Relative comparison of the fabric hand of array members (including for instance the comparison with a standard or blank) is a useful embodiment of this invention. Quantitative measurements of fabric hand are also provided by the present invention. The quantitative measurements allow comparison of fabric hand between the array members and other fabric materials not included in the array. As will be appreciated from the discussion elsewhere herein, in one particular embodiment, different material samples are compared with each other (quantitatively or qualitative, according to defined criteria) and their relative performance is ranked. In another particular embodiment, different material samples are compared to determine whether a specific response has occurred in any of the material samples. From the analysis of the materials, sub-sets of materials can be identified for further study or for production in bulk-scale quantities, such as for commercial application.

In regard to typical non-woven materials, and optionally to woven or other materials, it is preferred that fibers are aggregated in a generally cohesive manner. By way of example, to provide cohesion, it is preferred that the material is aggregated together with a suitable binder, (e.g., by applying in a wet state an emulsion containing waxes or polymers that, when dried, will form a continuous phase around the non-woven fibers). A particularly preferred binder for use in the present invention is an aqueous emulsion including a polymer (more preferably a copolymer). A more preferred binder also may include, a stabilizer, a surfactants, a crosslinking agent, or other suitable agent to impart mechanical strength to the system (e.g., once it has been exposed to elevated temperature (~150° C.)). The binder may add 1 to 99, preferably 5 to 50, more preferably 10–30 percentage weight to the fabric material.

What may vary from binder to binder are (1) the monomers used in the polymerization; (2) the order in which they are attached (random or blocky); (3) the surfactants; and (4) any other additives that may give the system unique characteristics (e.g., something that is sensitive to the presence of ions). One preferred binder includes an olefin, a vinyl ester, or a combination thereof, and an example of such a preferred binder is a copolymer of ethylene and vinyl acetate in an emulsion with various stabilizers. For more examples of suitable binders, see U.S. Pat. Nos. 4,605,589, 4,975,320 and 6,043,317. It is preferred that the binder should generally be uniformly distributed throughout the non-woven material, but it also may be randomly distributed. Such uniform distribution can be achieved using any number of conventional techniques. For example, the non-woven material immersed with the binder is passed through spaced opposing surfaces such as rubber-coated rollers with a self-adjusting gap to squeeze out any excess binder and provide uniform distribution. Depending on the nature of the binder (e.g., whether it contains any cross-linkable polymers), a drying step and/or a curing step can be used to process the non-woven material treated with the binder.

In accordance with the teachings of the present invention, it may also be possible to employ the present invention for analyzing the effects of the use of different binders from sample to sample. Thus, in an array of samples, binders employed may be the same or different.

It is generally contemplated that arrays of samples will be mounted for screening in or on a suitable support structure, namely a sample holder. Typically, the sample holder will have at least one and more preferably a plurality of openings defined therein. Thus, in one preferred embodiment, the sample size will be larger than the opening through which it will be forced by a probe during screening. It is preferred that the sample is at least about 2 times larger than the opening, more preferred at least about 5 times larger than the opening, and most preferred about 10 times larger than the opening. Typical sample sizes can range from about 8 mm to about 18 mm, more preferred from about 12 mm to about 18 mm, and most preferred from about 15 mm to about 17 mm. Larger diameters are also possible.

The Parallel Dynamic Mechanical Analyzer

Figure 11:
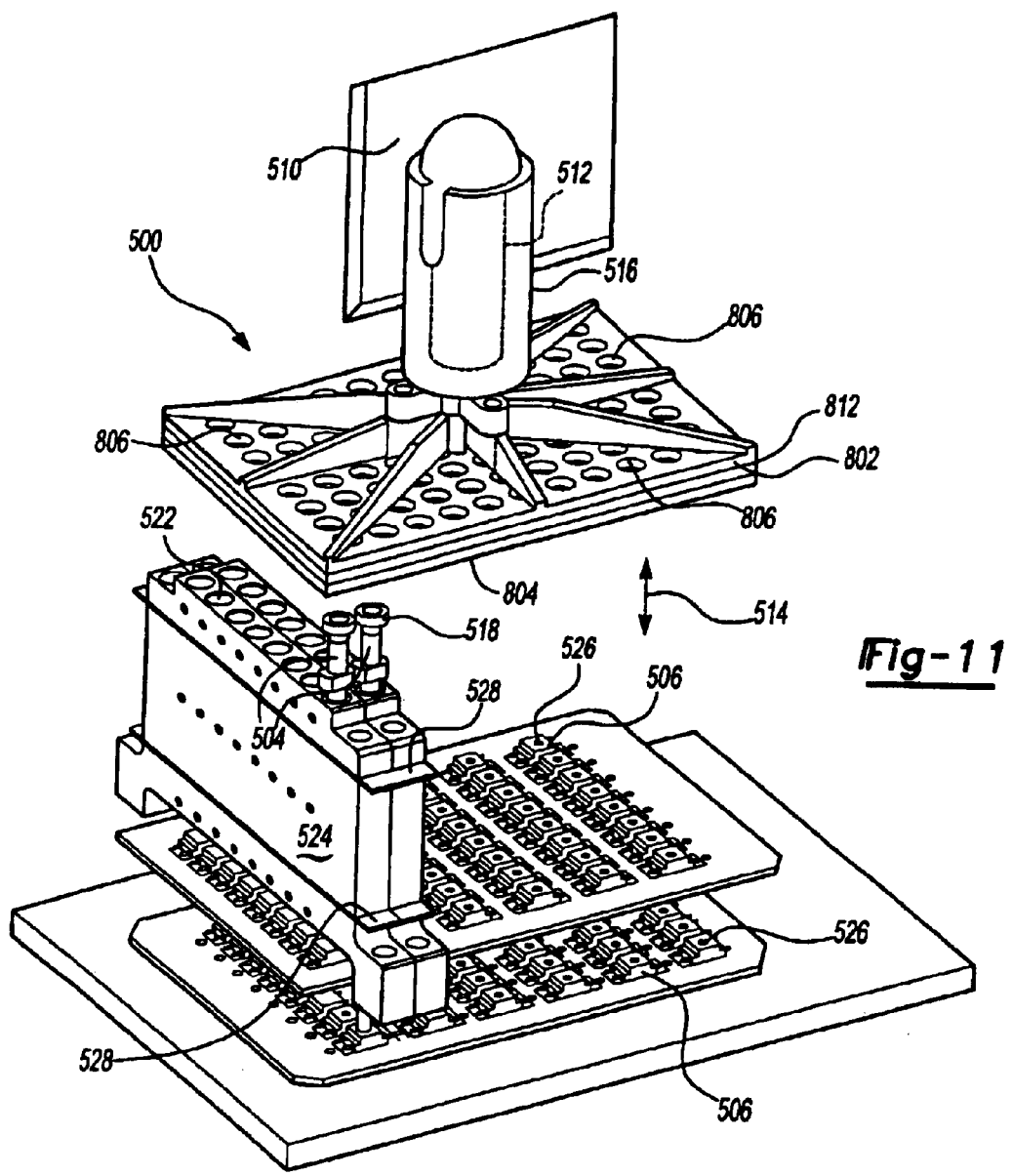
FIG. 11 shows a perspective view of one embodiment of a parallel dynamic mechanical analyzer that can be used for high throughput fabric handle screening.

FIG. 11 shows a perspective view of one instrument suitable for property analysis (i.e., screening), and specifically, a parallel dynamic mechanical analyzer (PDMA) 500 that can be used to conduct high throughput fabric handle screening of an array of fabric samples 630 by measuring responses of the array 630 to protrusions. Detailed description of the PDMA 500 is described in commonly owned and co-pending U.S. patent application Ser. No. 09/580,024 titled "Instrument for High Throughput Measurement of Material Physical Properties and Method of Using Same," filed on May 26, 2000, which is herein incorporated by reference. Generally, the PDMA 500 includes a sample holder 502 for containing the array 630, probes 504 for protruding the array 630, and sensors 506 (e.g., force sensors) for measuring the array's 630 responses to the protrusions. The sample holder may be a single integrated unit or a plurality of assembled components; likewise it may comprise a single opening in a first substrate, which is translatable (e.g., by robot arm) relative to a second substrate for holding sample.

Figure 12A:
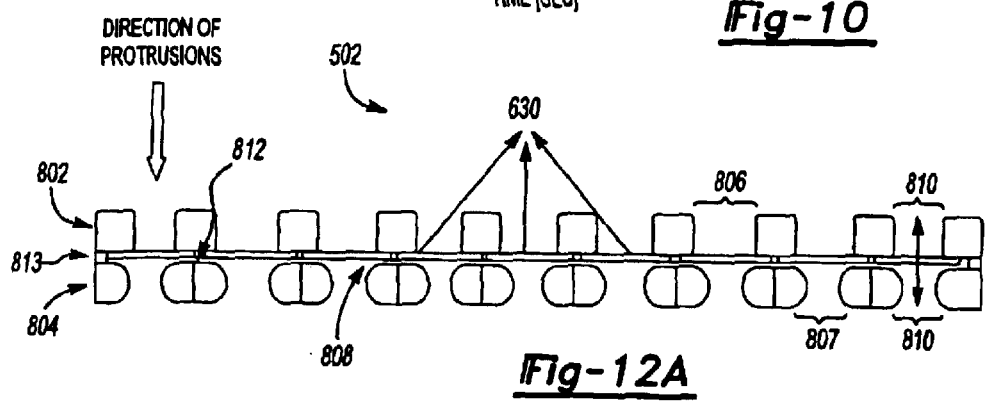
FIGS. 12A–B each shows a cross sectional view of a sample holder containing an array of fabric samples for fabric handle screening that can be used in a parallel dynamic mechanical analyzer for high throughput fabric handle screening.
Figure 12B:
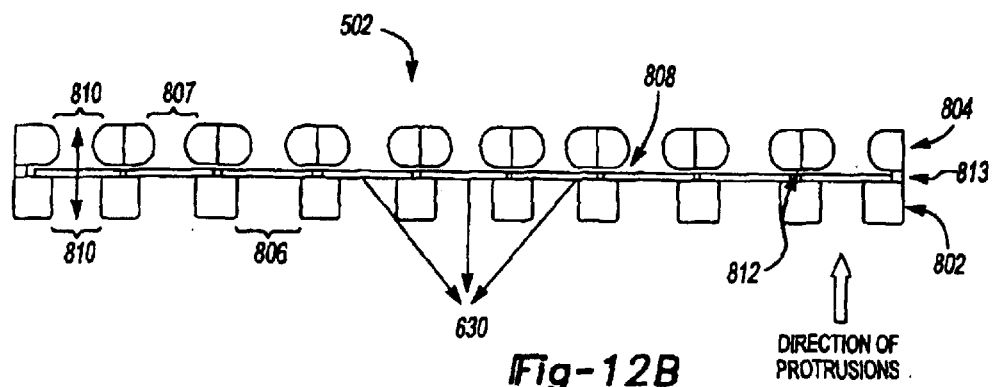

FIG. 12A shows a cross-sectional view of one preferred sample holder 502 which is comprised of a first plate 802 having a plurality of through-holes 806 and a second plate 804 having a plurality of openings 807 wherein the through-holes 806 and the openings 807 are aligned with each other forming tunnels 810 within the sample holder 502. Since the array 630 are protruded through the openings 807, their size and shape can affect the fabric handle measurements and are taken into consideration in measuring the fabric handle of the array 630. For instance, each of the openings 807 preferably is large enough for the array sample 630 to collapse upon itself, while still maintaining a portion of itself in physical contact with the walls of the opening 807 during the protrusions. Referring to FIG. 12A, one preferred leading edge 808 to the opening 807 must allows for a smooth transition for the sample 630 to transfer from a flat state to the bent and folded state which occurs during the protrusions. Thus, it is preferred that the opening 807 is constructed of a smooth material or coated with a smooth material (e.g., a plastic layer, a coating, or the like). Although the openings 807 can be any shape and/or size, it is preferred that they are funnel-shaped or otherwise a rounded or a tapered periphery with a diameter at the top of each funnel that is twice of the bottom diameter, and with the height of the sloped section at least equal to the height of the straight section. For examples of other preferred embodiments of the openings 807 that may be used during fabric handle screens, see FIGS. 12C–J. Other variations or combinations of such structures are also possible. The through-holes 806 can also be any shape or size as long as they do not restrict or inhibit the protrusions of the array 630 by the probes 504. Furthermore, depending on the direction of the protrusions, the first plate 802 may be placed above the second plate 804 with its openings 807 as shown in FIG. 12A, or vice versa, as shown in FIG. 12B.

Figure 12C:
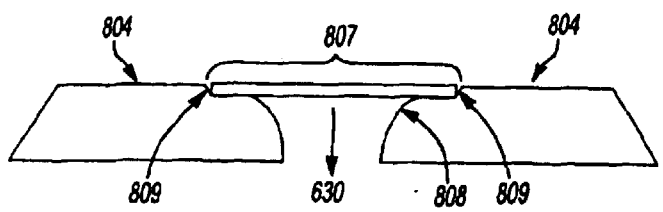

Referring to FIG. 12A, a gap of suitable size 812, e.g., preferably about 1 mm, more preferably about 3 mm, exists between the first plate 802 and the second plate 804. The gap 812 can be formed by any number of art disclosed techniques. For example, spacers 813 such as beads or two standard washers (e.g., 0.5 mm each) can be placed between the first plate 802 and the second 804 to create a gap of approximately 1 mm. The array 630 is placed between the first plate 802 and the second plate 804 of the sample holder 502 with the individual array samples 630 confined to specific locations 414 on the sample holder 502. Referring to FIG. 12C, it is preferred that each opening 807 is surrounded by an indentation 809 in the second plate 804 that restricts any horizontal movement of its respective sample 630. It is also preferred that there is a one to one correspondence between the specific locations 414 and the openings 807. Additionally, it is preferred that the samples 630 do not overlap each other but each sample 630 is sized to include and extend beyond the regions defined by the diameter of the opening 807. It is preferred that each sample 630 is at least about 2 times larger than the diameter of the opening 807, more preferred at least about 5 times larger than the diameter of the opening 807, and most preferred about 10 times larger than the diameter of the opening 807. The particular sample holder 502 shown in FIG. 11 and FIG. 12 contains an 8-by-12 rectangular array of fabric samples 630 located on 9 mm centers. However, the sample holder 502 can be designed to contain any number of samples in an array. For example, the sample holder 502 can be designed to contain 4 or more, 8 or more, 16 or more, 24 or more or 48 or more samples in an array. Those of skill in the art will appreciate that this is simply a matter of design choice and the invention herein is not limited to the specific embodiments described in detail.

The PDMA 500 generally has as many probes 504 as desired. For example there may be as many as there are samples in the array 630, although for clarity, FIG. 11 shows only two probes 504. In the embodiment shown in FIG. 11, the probes 504 have the same lateral spacing as the tunnels 810 or openings 807 so that one probe 504 is associated with one opening 807 or sample 630. Alternatively, the PDMA may employ fewer probes 504 than samples in the array 630, so that a group of probes 504 protrudes multiple samples 630. It is preferred that the PDMA 500 includes a translation mechanism capable of three-dimension motion, which is attached to this group of probes 504 or to the sample holder 502 to allow high throughput serial-parallel screening. Alternatively, there may be more probes 504 than samples in the array 630. Alternatively, there may be only one probe 504 and the PDMA 500 includes a translation mechanism capable of three-dimensional motion, which is attached to the single probe 504 or to the sample holder 502 to allow high throughput screening in a rapid serial fashion.

The PDMA 500 includes at least one actuator for moving the probes 504 and the samples 630 in relation to each other. In one preferred embodiment, the actuators are attached to the probes 504 and the samples 630 remain stationary. In another preferred embodiment, the actuators are attached to the sample holder 502 and the probes remain stationary. In yet another preferred embodiment, both the probes 504 and the sample holder 502 have actuators attached allowing them to both become non-stationary. In an exemplary preferred embodiment, the PDMA 500 includes first 510 and second 512 translation actuators for displacing the array 630 in a direction normal 514 to surfaces containing the array 630 and the ends 516 of the probes 504. The first translation actuator 510, which is attached to the sample holder 502 via a housing 516 that surrounds the second translation actuator 512, provides relatively coarse displacement of the sample holder 502. A useful first translation actuator 510 includes a motorized translation stage available from POLYTEC PI under the trade name M-126 Translation Stage, which has a translation range of 25 mm and a resolution of 0.1 $\mu$m. The second translation actuator 512, which is attached directly to the sample holder 502, provides relatively fine displacement of the sample holder 502. A useful second translation actuator 512 includes a preloaded piezoelectric stack available from Polytec PI under the trade name P-753 LISA Linear PZT Stage Actuator, which has a translation range of 30 (m and can provide a 100-N pushing force and a 20-N pulling force. The PDMA 500 typically controls the first 510 and second 512 translation actuators using a DC motor controller and an amplifier/position servo controller, respectively, which are linked to a suitable general-purpose computer (not shown). In an alternative embodiment, the first 510 translation actuator is mounted on an x-y translation stage (not shown), which allows movement of the sample holder 502 in a direction substantially parallel to the surfaces containing the array 630 and the ends of the probes 504. This latter embodiment is useful when the sample holder 502 must be moved laterally to align different groups of array samples 630 with the probes 504 during screening—i.e., when the PDMA employs fewer probes 504 than samples in the array 630 and the probes 504 are stationary.

Each of the probes 504 includes a test fixture 518 that contacts one of the sensors 506 through a solid or composite shaft 520 shown in phantom in FIG. 11. Each shaft 520 passes through an aperture 522 in an isolation block module 524 that separates the probe test fixture 518 from the sensor 506. For clarity, FIG. 11 shows only two isolation block modules 524, although this embodiment of the PDMA 500 ordinarily includes twelve such modules 524—one isolation block module 524 for each row of eight probes 504. Alternatively, the PDMA may include a single isolation block for separating the probe test fixtures 518 from the sensors 506. For reliable measurements, each test fixture 518 should contact its associated sample 630 in a specific location 108 on the sample holder 502. This requires a mechanism for locating the composite shaft 520 along a line extending from the center 526 of a particular sensor 506, normal to the surface of the array 630. Although conventional linear bearings can be used to align the composite shaft 520, friction between the linear bearings and the shaft 520 limits the displacement resolution at low force levels. In addition, the PDMA can also use air bearings, but the size and expense of air bearings often make them impractical for use with a PDMA employing relatively large numbers of probes 504.

FIG. 13, which illustrates the use of two flexure strips 550 to align the probes 504 with the samples 630, shows a cross-sectional view of one of the isolation block modules 524 as seen through a cutting plane containing centerlines of the apertures 522 shown in FIG. 11. The flexure strips 550 are sandwiched between generally planar surfaces of upper 552 and intermediate 554 segments of the isolation block module 524 and between generally planar surfaces of the intermediate 554 and lower 556 segments of the isolation module 524. The two flexure strips 550 shown in FIG. 13 comprise relatively thin (from about 10 $\mu$m to about 100 $\mu$m) rectangular membranes having spaced-apart holes that are substantially aligned with each composite shaft 520 within the apertures 522 of the isolation block modules 524.

As shown in FIG. 13, the composite shaft 520 is comprised of a rigid, substantially cylindrical core 558 and a thermally insulating outer sheathing having upper 560, intermediate 562, and lower 564 sections that are threaded onto the core 558. When installed in the apertures 522, the abutting ends of the upper 560 and intermediate 562 sections of the sheathing and the intermediate 562 and lower 564 sections of the sheathing lie in planes containing the two flexure strips 550. Since the diameters of the core 558 and the holes in the flexure strips 550 are about the same, the periphery of the holes are clamped between the abutting ends of the upper 560, intermediate 562, and lower sections of the sheathing. The flexure strips 550 are also clamped along the periphery of each aperture 522, adjacent interfaces between the upper 552, intermediate 554, and lower segments 556 of the isolation block module 524. The resulting clamped membranes or diaphragms 566, which span annular gaps 568 between the shafts 520 and the isolating block module 524, support and align the probes 504.

The geometry of the diaphragms 566 makes each of the flexure strips 550 compliant for displacements normal 514 to the surface supporting or containing the array 630, but mechanically stiff for displacements parallel to the array 630. The use of two flexure strips 550 also makes each combination of shaft 520 and diaphragms 566 mechanically stiff for angular displacements away from the direction normal 514 to the surface of the array 630. Moreover, through proper selection of materials and dimensions, the flexure strips 550 exhibit effective spring constants—for displacements normal 514 to the array 630—substantially less than effective constants of the sensors 506. In this way, the flexure strips 550 ordinarily exert minimal influence on the measured responses to protrusions, unless they are used to "pre-load" the sensors 506 as discussed below. Useful materials for the flexure strips 550 include metallic and polymeric films. For example, one particularly useful flexure strip material is polyimide film, which is available from DuPont under the trade name KAPTON in thickness ranging from about from about thirteen $\mu$m to about one hundred twenty five $\mu$m. Other useful flexure materials include stainless steel foil, diaphrams (in general) and corrugated bronze, for example, the flexure may be mechanically machined stainless steel. Since the effective spring constants of the diaphragms 566 and typical sensors 506 are temperature-dependent, the use of thermally insulating sheathing 560, 562, 564 on the shafts 520 permits the PDMA 500 to vary the temperature of the arrays 630 without significantly affecting the measured response.

For the high throughput fabric handle screening, it is preferred that the PDMA 500 employs a probe 504 having a blunt end (not shown) for protruding the array 630. Alternatively, the probe 504 can be equipped with a blunt end test fixture 518 for protruding the array 630. The PDMA 500 may provide a mechanism for removing and securely attaching the test fixtures 518. Suitable attachment mechanisms include mechanical and electromagnetic couplings, as well as devices employing permanent magnets. FIG. 14 shows a close-up cross sectional view of the probe 504 shown in FIG. 13, and illustrates the use of a permanent magnet 590 to attach the test fixture 518 to the threaded core 558 of the composite shaft 520. As shown in FIG. 14, the probe 504 includes a base 592 having first 594 and second ends 596 that adjoin, respectively, the test fixture 518 and the upper section 560 of the thermally insulating outer sheathing. A substantially cylindrical bore 598 extends partway into the base 592 and is sized and threaded to connect the core 558 of the shaft 520 to the second end 596 of the base 592. The test fixture 518 is removably attached to the first end 594 of the base 592 by magnetic flux originating from the permanent magnet 590 that is embedded in the base 592 of the probe 504. A tubular magnetic shield 600, which typically has a lower modulus than either the probe base 592 or the permanent magnet 590, is wedged into an annular space between the probe base 592 and the permanent magnet 590. The shield 600, which helps secure the magnet 590 within the probe base 592, extends outward from the first end 594 of the base 592 and mates with a substantially circular slot 602 formed in the test fixture 504. The slot 602 is sized to receive the tubular shield 600 with minimal interference, and the shield 600 has a tapered end 604 that helps guide it into the slot 602 during attachment of the test fixture 518 to the probe base 592. In the embodiment shown in FIG. 14, the test fixture 518 and the test fixture 518 and the probe base 592 include flanges 606, 608 for accessing them during removal or attachment.

As can be seen in FIG. 14, the test fixture 518, the base 592, and the shield 600 enclose the permanent magnet 590, which helps minimize stray magnetic flux that may influence sample measurements of nearby probes 504. Generally, the probe 504 components are made from materials having a high magnetic permeability—a relative permeability substantially greater than unity—to ensure effective magnetic shielding. Suitable materials include nickel-iron alloys containing copper, molybdenum, or chromium and mixtures thereof. A particularly useful shielding material is available under the trade name HI-PERM 49 from Carpenter Technology. Other useful shielding materials include cold-rolled steel that has been chrome-plated to resist corrosion. The permanent magnet 590 should be fabricated from a material that provides sufficient force to secure the test fixture 518 to the probe base 592 during screening. Useful permanent magnets 590 include samarium cobalt magnets, ceramic ferrite magnets, aluminum-nickel-cobalt magnets, and neodymium-iron-boron magnets.

FIG. 15 illustrates interactions of the probes 504, the sensors 506, and the array of fabric samples 630. FIG. 6 shows a cross sectional view of the PDMA 500 of FIG. 11 taken from a plane that cuts through the two isolation block modules 524 and contains centerlines of two adjacent probes 504. During screening, each test fixture 518 portion of the probes 504 interacts with an individual array sample 630, which is positioned at a specific location 414 of the sample holder 502 over an opening 807. Movement of the sample holder 502 in a direction normal 514 to the surface of the array 630 results in forces that are transmitted to the sensors 506 via each probe test fixture 518, probe base 592, and composite shaft 520. Each composite shaft 520, which includes a rigid core 558 and thermally insulating outer sheathing 560, 562, 564, contacts the force sensor 506 directly or indirectly as discussed below.

The relatively large footprint of each sensor 506 shown in FIG. 15 makes it impracticable to mount all of the sensors 506 on a single plane while maintaining 9 mm spacing between centers 526 of adjacent sensors 506. Of course, using sensors with smaller footprints may allow for mounting in a single plane. To provide 9 mm spacing, the PDMA 500 employs sensors 506 mounted on first 632 and second 634 sensor boards, which rest on upper 636 and lower 638 rigid support plates, respectively. Both support plates 636, 638 include holes that extend from top surfaces 640, 642 of the plates 636, 638 to bottom surfaces 644, 646 of the plates 636, 638. The holes are arrayed on 9 mm centers, and are either threaded or non-threaded. Non-threaded holes 648 in the upper support plate 636 are substantially aligned with through-holes 650 in the first sensor board 632. The non-threaded holes 648 and the through-holes 650 are sized to provide passageways for rods 652 that transmit forces from the composite shafts 520 to sensors 506 mounted on the second (lower) sensor board 634. The PDMA 500 thus maintains the most preferred spacing by distributing the force sensors 506 among two boards 632, 634—thereby doubling the surface area available to mount the force sensors 506—and by arranging the sensors 506 so their centers 526 are 9 mm apart when projected on the surface of the array 630. When using smaller sensors or when 9 mm spacing is not desired, the PDMA may dispense with one of the two sensor boards. As many sensor boards as is practical for a particular embodiment may be employed.

Figure 16:
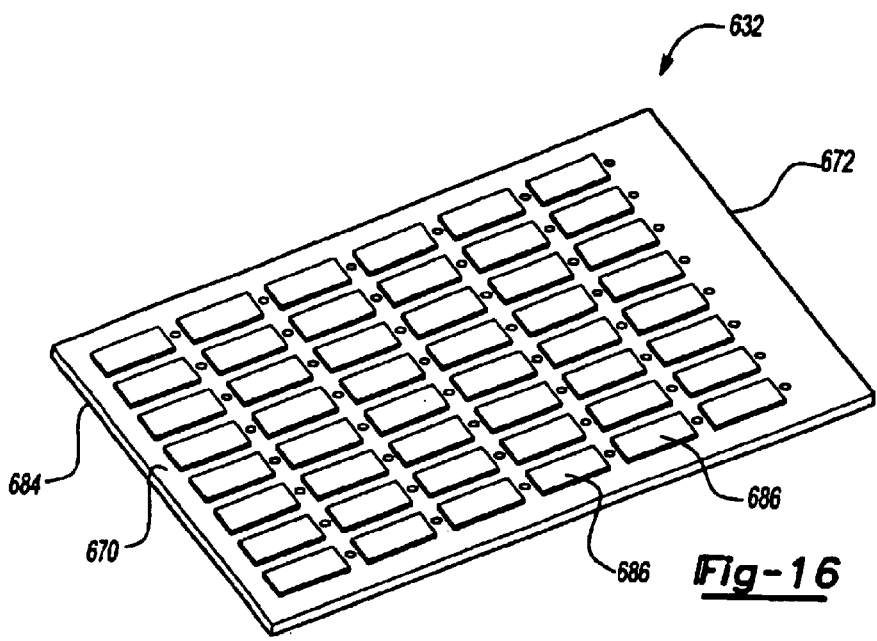
FIG. 16 shows a perspective bottom view of one of the sensor boards in a parallel dynamic mechanical analyzer.
Figure 17:
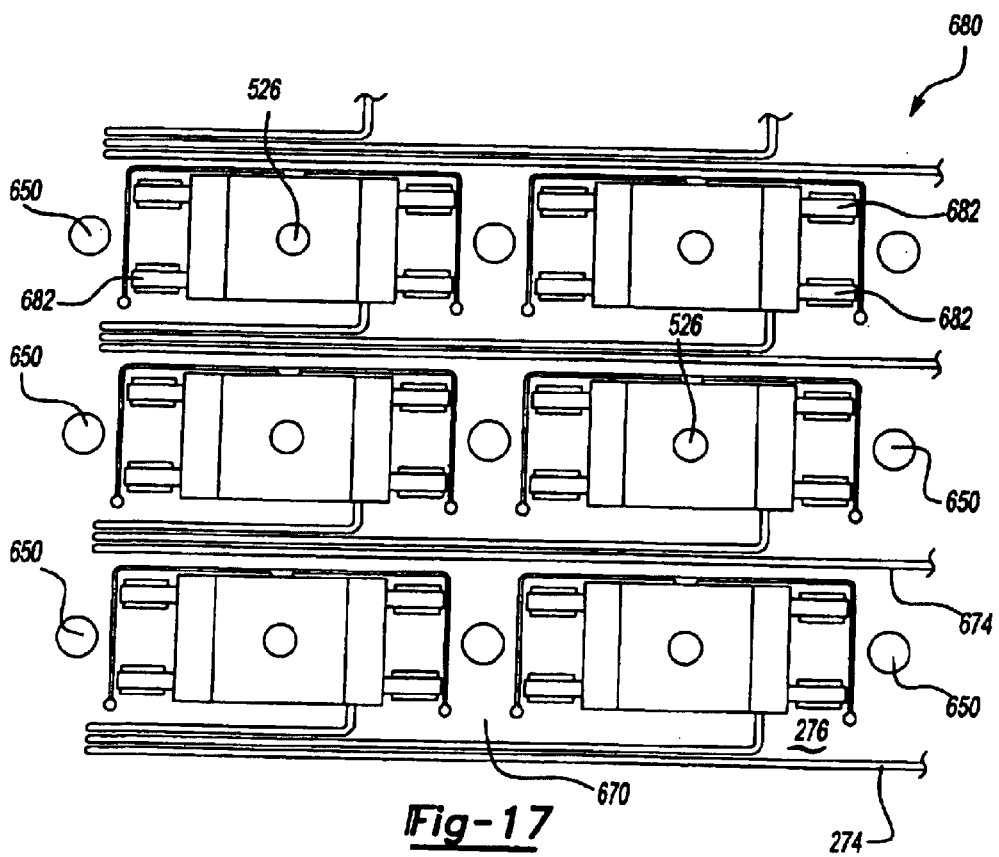
FIG. 17 shows a top view of a portion of one of the sensor boards in a parallel dynamic mechanical analyzer.

FIG. 16 and FIG. 17 provide further details of the sensors 506 and sensor boards 632, 634, showing respectively, a bottom perspective view and a close-up top view of the first sensor board 632. The first 632 and second 634 sensor boards generally comprise a flexible multi-layer dielectric sheet 670 (e.g., polyimide) and a rigid frame 672 (e.g., FR-4 epoxy glass laminate) that is bonded to the periphery of the dielectric sheet 672. Electrically conductive traces 674 are embedded on top 676 or bottom surfaces 278 of the dielectric sheet 670, or between layers of the flexible sheet 670, forming a double-sided flex circuit 680. Each sensor 506 is mounted on the top surface 676 of the flex circuit 680, and leads 682 on the sensors 506 are connected to conductive traces 674 that terminate at a standard card edge connector 684. Conventional ribbon cables can be used to link the card-edge connector 684 with peripheral recording and control devices (not shown) allowing communication between the sensors 506 and the peripheral devices.

As shown in FIG. 16, the first 632 and second 634 sensor boards include generally planar stiffeners 686 (e.g., FR-4 epoxy glass laminates) attached to the bottom surface 278 of the sensor boards 632, 634 directly below the sensors 506. Each of the stiffeners 686 has about the same footprint as the sensors 506, and helps distribute loads on, and prevent bending of, the sensors 506. Note however, the stiffeners 686 do not prevent movement of the sensors 506 in a direction normal 514 to the array 630 since the sensors 506 are mounted on the flexible dielectric sheet 670. Although other embodiments can use rigidly-mounted sensors, the PDMA 500 shown in FIG. 11 uses sensors 506 mounted on the flex circuit 680 to allow "pre-loading" of the sensors 506 as discussed below. Pre-loading may of course be performed by other methods, which those of skill in the art will appreciate from a review of this specification. Furthermore, a detailed discussion of "pre-loading" is set forth in the commonly owned and co-pending U.S. patent application Ser. No. 09/580,024 titled "Instrument for High Throughput Measurement of Material Physical Properties and Method of Using Same," filed on May 26, 2000, which has been incorporated by reference.

The first sensor board 632 shown in FIG. 17 also includes a plurality of through-holes 650 that are located between the sensors 506. Following assembly of the PDMA 500, the through-holes 650 are substantially aligned with unthreaded holes 648 in the upper support plate 636 (FIG. 15). As noted above, the unthreaded holes 648 in the upper support plate 636 provide passageways for rods 652 that transmit forces from the composite shafts 520 to sensors 506 mounted on the second (lower) sensor board 634. Thus, the centers 526 of the sensors 506 and the through-holes 650 of the first sensor board 632 are arrayed on 9 mm centers.

Referring to FIGS. 15–17, threaded holes 288, 690 in the upper 636 and lower 638 support plates are sized to receive set-screws 692 that the PDMA 500 can use to pre-load each of the sensors 506 mounted on either the first 632 or second 634 sensor boards. As noted in the description of FIG. 13, the flexure strips 550 used to align the probes 504, are compliant for displacements normal 514 to the plane containing the array 630, but are mechanically stiff for displacements in other directions. Moreover, the effective spring constants of the flexure strips 550 are substantially less than the spring constants of the sensors 506 so that the flexure strips 550 ordinarily exert minimal influence on the measured responses of the array 630 to protrusions. However, since the sensors 506 are mounted on the flex circuit 680, the set-screws 692 can apply a force to the stiffeners 686 and the sensors 506 in absence of a force on the test fixture 518. A force recorded by the sensors 506 will therefore be the sum of the force acting on the test fixture 518 and the pre-load force. Since many commercial force sensors can detect only tensile or compressive loads, pre-loading permits a compressive sensor to detect small tensile loads, or a tensile sensor to record small compressive loads, expanding the capabilities of the PDMA 500. Note that the lower support plate 638 and the second sensor board 634 both include unthreaded holes 694, 296 that provide access to the setscrews 692 in the upper support plate 636.

The PDMA 500 can use a wide variety of sensors 506, including miniature force sensors. Most of the sensors 506 incorporate signal conditioning electronics. Suitable force sensors include piezoresistive micromachined silicon strain gauges that form a leg of a conventional Wheatstone bridge circuit. A useful low-compliant force sensor is available from Honeywell under the trade name FSL05N2C. The Honeywell force sensor has a 500-g range (4.9 N full scale), which is suitable for most of the screening methods described in subsequent sections. As noted earlier, many force sensors can tolerate only modest variation in temperature without compromising accuracy and precision. The use of a composite shaft 520 having an insulating sheathing 560, 562, 564 (FIG. 13) permits substantial temperature variation of the array 630 without significantly affecting the temperature and accuracy of the sensors 506.

In an alternative embodiment, force sensors are incorporated into the flexure strips 550 by placing strain gages on the diaphragms 566 (FIG. 13). Strain resulting from the application of a known force—typically a deadweight load applied to the rigid shaft 520—is recorded and used to develop a calibration curve for the force sensor. The principal disadvantage of this approach is the extensive signal conditioning requirements associated with strain gage measurements.

Referring again to FIG. 11 and FIG. 13, the PDMA 500 may include an environmental chamber (not shown) that encloses the sample holder 502, the probes 504, and the upper 552 or intermediate 554 segments of the isolation block modules 524 that control the environment (e.g., temperature, humidity, etc.) of the samples 630. The chamber may be filled with a gas of known composition to study its influence on the fabric handle of the samples 630. Generally, the annular gap 568 between the composite shafts 520 and the cylindrical apertures 522 is minimized to limit the flow of gas out of the isolation block modules 524. In addition, the flexures 550 in the annular gaps 568 restrict gas efflux from the isolation block modules 524.

Alternatively, the environmental chamber may comprise a substantially gas-tight enclosure that surrounds the sample holder 502, the probes 504, the isolation block modules 524, and the sensors 506. The enclosure may be further separated into two compartments—one that encloses the sample holder 502 and the samples 630, and one that encloses the sensors 506 and the isolation block modules 524. The latter embodiment allows blanketing the sample holder 502 and the samples 630 with a first gas that is different than a second gas blanketing the sensors 506. In this way, the PDMA can vary the environment of the samples 630 independently of the sensors 506, while maintaining the sensors 506 at conditions different than or the same as the laboratory environment.

The environmental chamber may include devices for regulating and/or monitoring the temperature of the samples 630. Useful devices include one or more heating or cooling elements placed within a gas stream that feeds the environmental chamber containing the array 630. Other useful devices include an array of radiant heaters positioned adjacent to the samples 630. Alternatively, the PDMA 500 may include resistance heaters or thermoelectric devices that are attached to the sample holder 502, which heat or cool individual or groups of samples in the array 630. The PDMA 500 may also include devices such as thermocouples, thermistors, or resistive thermal devices (RTD) for monitoring the temperature of individual samples 630. In some embodiments, the PDMA 500 includes a temperature controller, such as a data acquisition board, for subjecting the array 630 to a desired temperature-time profile. The temperature controller automatically adjusts the power supplied to the heating and cooling devices in response to signals received from the temperature monitoring devices. Typically, software running on an external computer communicates and coordinates functions of the temperature controller and the temperature monitoring devices.

Parallel Dynamic Mechanical Analyzer Control and Data Acquisition

Figure 18:
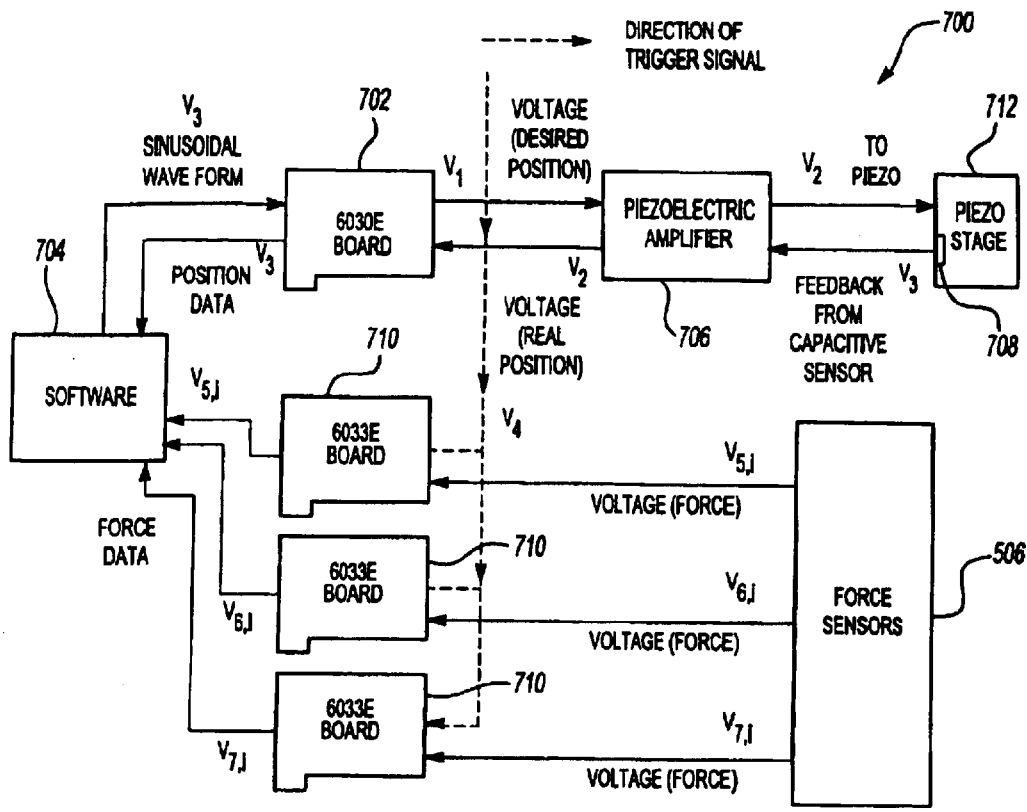
FIG. 18 is a flow chart for the data acquisition control for a parallel dynamic mechanical analyzer.

FIG. 18 shows schematically a system 700 for data acquisition and control of the PDMA. As noted in the discussion of FIG. 11, the PDMA 500 includes first 510 and second 512 translation actuators for displacing the array 630 (FIG. 15) in a direction normal 514 to the probes 504. The first translation actuator 510 provides relatively coarse displacement of the sample holder 502; it positions the samples 630 near the probe 504 test fixtures 518, and can be regulated using a DC motor controller (not shown). The second translation actuator 512 provides relatively fine displacement of the sample holder 502 and is responsible for carrying out protrusions of the individual samples 630.

The second translation actuator 512 shown in FIG. 18 comprises a piezoelectric translation stage. A primary data acquisition board 702 (e.g., National Instruments 6030E), which is located in an external computer 704, controls the operation of the second translation actuator 512. The primary board 702 generates a voltage, $V_1$, which is proportional to the desired displacement of the actuator 512 (and sample holder 502). This voltage is fed to a piezoelectric amplifier 706 that monitors the position of the actuator 512 via a capacitive position sensor 708. In response to $V_1$, the piezoelectric amplifier 706 varies the charge, $V_2$, which it supplies to the actuator 512 to move the sample holder 502 to its desired position. The position sensor 708 generates a voltage, $V_3$, which is read by the amplifier 706 and indicates the actual position of the second translation actuator 512.

As shown in FIG. 18, the primary data acquisition board 702 and the external computer 704, respectively, read and record $V_3$. In response to the value of $V_3$, the primary board 702 updates $V_1$ as necessary and generates a timing pulse, which triggers acquisition of $V_3$ from the position sensor 708, thereby synchronizing signals $V_1$ and $V_3$. The acquisition of $V_3$ also generates a second timing pulse, $V_4$, which triggers acquisition of voltages $V_{5,i}$, $V_{6,i}$, and $V_{7,i}$, from the sensors 506. Secondary data acquisition boards 710 acquire $V_{5,i}$, $V_{6,i}$, and $V_{7,i}$, where subscript refers to a particular data line (channel) of the data acquisition board 710. Thus, measurements of the response of the array 630 to protrusions are synchronized with the motion of the second translation actuator 512 (and sample holder 502), and the measurement of the actuator 512 position. Although the system 700 shown in FIG. 8 uses three secondary data acquisition boards 710 having 32 channels each, the number of boards 710 will depend on the number of available data channels and sensors 506. Alternatively, the PDMA may use a single data acquisition board to control the actuator 512 position and to acquire sensor 506 data, assuming the board has a sufficient number of data channels and output signals.

Software running on the computer 704 coordinates the activities of the boards 702, 710 and allows the user to specify screen parameters including positions of the first 510 and second 512 translation actuators at any given time, the number of samples 630, and so on.

General Methodology

The methodology for high throughput fabric handle screening used in this experiment generally includes the following steps: (1) providing a plurality of samples of non-woven materials; (2) aggregating the materials in a binder; (3) placing the samples on a sample holder having a plurality of openings with smooth edges; (4) protruding the samples; (5) measuring the response of each sample; (6) comparing the samples relating to each other; (7) identifying the samples that meet predetermined criteria and/or ranking the samples based upon their individual performance; and (8) preparing bulk scale quantities of a material or materials based upon the results of this high throughput fabric handle screening.

Figure 10:
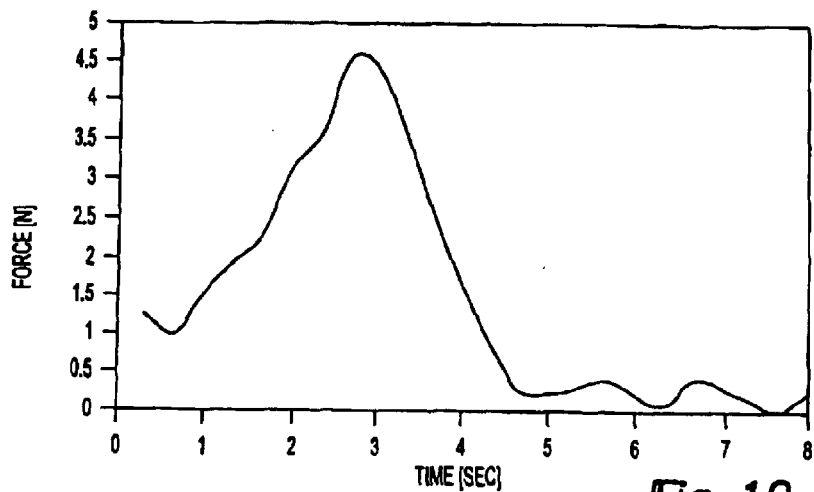
FIG. 10 shows a load-displacement curve obtained during fabric handle screening from an individual fabric sample of an array.

Method of Screening Fabric Handle Using the Parallel Dynamic Mechanical Analyzer Referring to FIG. 12, the method of screening fabric handle using the PDMA 500 begins with placing the array of fabric samples 630 between the first plate 802 and the second plate 804 of the sample holder 502 with the individual samples 630 confined to specific locations 414 on the sample holder 502. Thereafter, the samples 630 in the sample holder 502 are translated in a direction normal to the ends 516 of the probes 504. Alternatively, as discussed above, the translation can be achieved by the probes 504 in a direction normal to the sample holder 502 or both by the probes 504 and the sample holder 502 in a direction normal to both. The translation is preferred to be conducted at a constant speed controlled by the system 700. It is also preferred that the speed is less than 10 mm per second but greater than about 1 mm, but more preferably about 5 mm per second. As the samples 630 continue to translate in the direction normal to the ends 516 of the probes 504, they first contact the blunt ends of the probes 504 through the throughholes 806 of the first plate 802 and then begin to fold and are eventually, and preferably completely, forced through the openings 807 of the second plate 804. This typically requires, but is not limited to, a translation of at least about 15 to 20 mm. The translation from the point of first contact between the blunt ends of the probes 504 and the samples 630 should be a distance at least equal to, and preferably greater than, the radius of the samples 630. During the protrusions by the probe 504, each sample 630 is preferably first contacted by the probe 504 at its center point and then becomes folded, sheared, bent, compressed, elongated, and rubbed against the interior wall of the opening 807. The force sensors register all the forces transmitted through the probe 504 and the information is transferred to the system 700. The output is a trace of force versus position of the sample holder 502 providing a load-displacement curve as shown in FIG. 10.

In a preferred embodiment, the probes 504 have about the same lateral spacing as the tunnels 810 and/or the openings 807 so that there is a one-to-one correspondence between the individual probes 504 and the samples in the array 630. In addition, since the array 630 and the ends of the probes 504 also define two generally planar surfaces, the system can protrude all of the array samples 630 simultaneously by displacing the array 630 (sample holder 502) and/or the probes 504 in a direction normal to the two surfaces. If adapted to protrude all of the array samples 630 simultaneously, the system may include a rectilinear translation stage that is attached to the sample holder 502 or the probes 504.

In other embodiments, the system may protrude individual or groups of array samples 630 in a rapid serial fashion. In these embodiments, the system may include a translation mechanism capable of three-dimensional motion, which is attached to a single probe 504, to a group of probes 504, or to the sample holder 502.

The Automated Rapid Serial System

Figure 19:
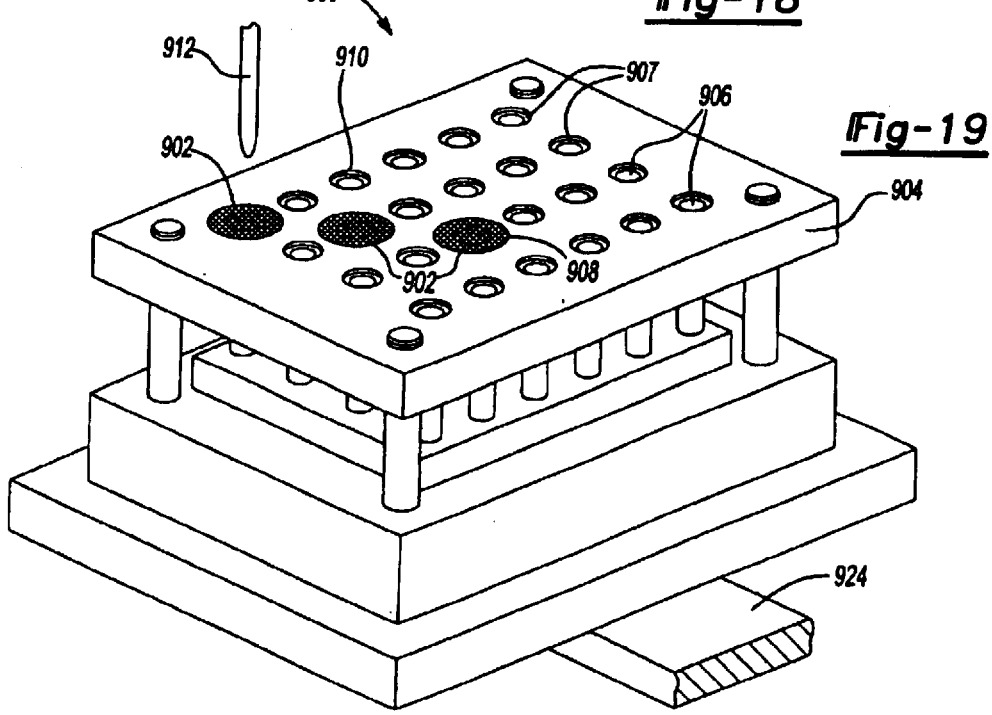
FIG. 19 shows a perspective view of one embodiment of an automated rapid serial system that can be used for high throughput fabric handle screening.

FIG. 19 shows a perspective view of another instrument suitable for screening, and specifically, an automated rapid serial system (ARSS) 900 that can be used to conduct high throughput fabric handle screening of an array of fabric samples by measuring responses of the array samples to protrusions. The ARSS 900 can be configured for use with parallel, serial or serial-parallel protocols. In a most preferred embodiment, the ARSS 900 can be configured for use in a rapid serial fashion with a high sample screening throughput. Generally, ARSS 900 includes a variety of robotic instruments for automatically or programmably providing predetermined motions for protruding an array of fabric samples 902 according to a predetermined protocol. ARSS 900 may be adapted or augmented to include a variety of hardware, software or both to assist it in determining the fabric hand of the array members. Hardware and software for augmenting the robotic systems may include, but are not limited to, sensors, transducers, data acquisition and manipulation hardware, data acquisition and manipulation software and the like. Exemplary robotic systems are commercially available from CAVRO Scientific Instruments (e.g., Model NO. RSP9652) or BioDot (Microdrop Model 3000).

Figure 20:
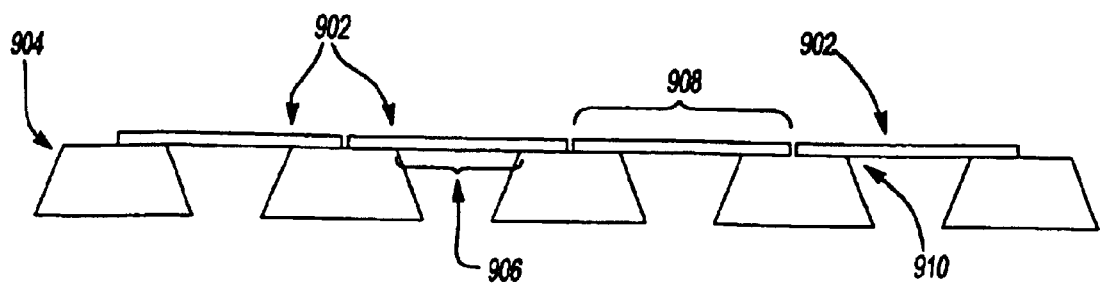
FIG. 20 shows one preferred embodiment of a sample holder that can be used in the automated rapid serial system.

Referring to FIG. 19 and FIG. 20, the ARSS 900 includes a sample holder 904 having a plurality of openings 906. The array of fabric samples 902 is preferably confined to specific locations 908 located on the sample holder 904 with one to one correspondence between the specific locations 908 and the openings 906, and that the array samples 902 do not overlap each other but include and extend beyond the regions defined by the diameter of the openings 906. It is also preferred that each opening 906 is surrounded by an indentation 907 in the sample holder 904 that restricts any horizontal movement of its respective sample 902. This indentation is similar to the indentation in the second plate 804 shown in FIG. 12C for the PDMA 500 instrument.

It is further preferred that each sample 902 is at least about 2 times larger than the diameter of the opening 906, more preferred at least about 5 times larger than the diameter of the opening 906, and most preferred about 10 times larger than the diameter of the opening 906. The particular sample holder 904 shown in FIG. 19 and FIG. 20 contains a 4-by-6 rectangular array of fabric samples 902 located on 18 mm centers. However, the sample holder 904 can be designed to contain any number of samples in an array. For example, the sample holder 904 can be designed to contain 4 or more, 8 or more, 16 or more, or 48 or more samples in an array. The size and shape of the openings 906 can affect the fabric handle measurements and are taken into consideration in measuring the fabric handle of the array samples 902. For instance, the opening 906 need to be large enough for the sample 902 to collapse upon itself naturally but still has a portion of itself in physical contact with the walls of the opening 906 during the protrusions. Referring to FIG. 20, one preferred leading edge 910 to the opening 906 allows for a smooth transition for the sample 902 to transfer from a flat state to the bent and folded state which occurs during the protrusions. Thus, it is preferred that the opening 906 is constructed out of a smooth material or coated with a smooth material (e.g., a plastic layer, a coating, or the like). Although the openings 906 can be any shape and/or size, it is preferred that they 906 are funnel-shaped or otherwise a rounded or a tapered periphery with a diameter at the top of each funnel that is twice of the bottom diameter, and with the height of the sloped section at least equal to the height of the straight section. The alternative embodiments of openings shown in FIGS. 12C–J are also applicable for the ARSS 900. Alternatively, the sample holder 904 can have the same specifications as the sample holder 502 described above for the PDMA 500.

The ARSS 900 also includes a probe 912 (or other similarly functioned device) having a blunt end for protruding the array 902. Alternatively, the probe 912 can be equipped with a blunt end test fixture 518 for protruding the array 902. The ARSS 900 can generally include as many probes 912 as desired, for example there may be as many as probes 912 as there are samples in the array 902 and in a preferred embodiment, the probes 912 have about the same lateral spacing as the openings 906 so that one probe 912 is associated with one opening 906 or sample 902. Alternatively, the ARSS may employ fewer probes 912 than samples in the array 902, so that a group of probes 912 protrudes multiple samples 902, or there may be more probes 912 than samples in the array 902. Alternatively, there may be only one probe 912 and the ARSS 900 includes a translation mechanism capable of three-dimensional motion, which is attached to the single probe 912 or to the sample holder 904 to allow high throughput screening in a rapid serial fashion.

The ARSS 900 includes actuator(s) 914 for moving the probe(s) 912 and the samples 902 in relation to each other. In one preferred embodiment, the actuator 914 is attached to the probe 912 and the samples 902 remain stationary. In another preferred embodiment, the actuator 914 is attached to the sample holder 904 and the probe 912 remains stationary. In yet another preferred embodiment, both the probe 912 and the sample holder 904 have actuators 514 attached allowing both of them to translate.

Optionally, the ARSS 900 further includes an environmental chamber for controlling the environment (e.g., temperature, humidity, etc.) of the array. An example of a suitable environmental chamber is a thermal jacket for heating and cooling the array 902 as desired (e.g., preferably between −100° C. and 200° C.). One preferred thermal jacket includes passages for receiving a heated or cooled fluid such as liquid nitrogen, water, steam or other suitable fluid from a fluid supply. The fluid from the fluid supply may be pumped to the thermal jacket with a pump that is controlled by a controller.

Method of Screening Fabric Handle Using the Automated Rapid Serial System

Referring to FIGS. 19–20, the method of screening fabric handle using the ARSS 900 begins with placing the array of fabric samples 902 in specific locations 908 on the sample holder 904. Thereafter, the robot 520, preferably controlled by the robot control software 918, translates the probe 912 into contact with each sample in the array 902. Alternatively, as discussed above, the translation can be achieved by the sample holder 904 or by both the probe 912 and the sample holder 904. The translation is preferred to be conducted at a constant speed controlled by the ARSS 900. It is also preferred that the speed is less than 10 mm per second but greater than about 1 mm, but more preferably about 5 mm per second. After initial contact between the probe 912 and the sample 902, continued translation causes the sample 902 to fold and is eventually forced through the opening 906 as the probe 912 protrude the sample 902. The protrusion typically requires, but is not limited to, a translation of at least about 15 to 20 mm. The translation from the point of first contact between the blunt end of the probe 912 and the sample 902 should be a distance at least equal to, and preferably greater than, the radius of the sample 902. During the protrusions by the probe 912, each sample 902 is preferably first contacted by the probe 912 at its center point and then becomes folded, sheared, bent, compressed, elongated, and rubbed against the interior wall of the opening 906. Response measuring hardware register all the forces transmitted through the probe 912 and the information is transfer to data acquisition hardware/software. Thereafter, robot control software data acquisition hardware/software or both transmit data to the protocol design and execution software such that information about each sample in the array 902 may be matched with its responses to the protrusions and transmitted at data to a database. Once the data is collected in the database analytical software may be used to analyze the data, and more specifically, to determine the mechanical properties associated with the fabric hand of each sample in the array 902 or the data may be analyzed manually. Generally, the output is a load-displacement curve as shown in FIG. 10.

Interpretation of the Load-Displacement Curve

The load-displacement curve obtained during the high throughput fabric handle screening methods discussed above contains information about various mechanical properties associated with fabric handle such as bending modulus, shear stiffness, compression, friction, and extensibility. Due to the extreme complexities of the interactions of these mechanical properties throughout the duration of the screen, extraction of the various properties from the curve is extremely difficult. See Pan, Ning and Yen, K. C., "Physical Interpretations of Curves Obtained Through the Fabric Extraction Process for Handle Measurement," *Textile Res. J.* 65(5), 279–290 (1992). The maximum force reached during the protrusion is thus taken to be representative of the overall fabric handle, incorporating all of the various mechanical properties into one value.

EXAMPLE

An example of the present invention is performed upon an airlaid non-woven fabric materials. The experiment begins with cutting an airlaid non-woven fabric material into a rectangle approximately 2"×1" in size and sandwiching between two pieces of polyester scrim to hold the fabric material together during the padding process. The fabric material is placed into a shallow container and soaked with 300 ml of binder solution (generally an emulsion). The binder solution is diluted down sufficiently so that the percent weight added on to the non-woven fabric material during this process is about 15%. The wet fabric material is passed between two rubber-coated rollers with a self-adjusting gap to squeeze out the excess liquid and ensure a uniform distribution of polymer solids throughout the fibers. The sample is dried at 110° C. for approximately 10 minutes, either with or without the scrim. Depending on the emulsion (i.e., is there cross-linker in the system), there is a curing step following the drying step at 130° C. for 5 minutes. Thereafter, the fabric material is cut to form 4 fabric samples with each sample being a 2 cm diameter circle. This process of preparing the fabric samples is repeated 6 times, each time with a different binder to yield an array of 24 fabric samples. The fabric samples are then arranged in a 4×6 array and centered over the funnel-shaped openings in the sample holder. For the 4×6 array, the outer lip of each of the funnel-shaped openings is 12 mm in diameter, and the inner opening is 6 mm in diameter. The centers of the openings are spaced 18 mm apart. After the array is placed onto the sample holder, they are then placed onto a cantilever-type load cell with a maximum allowable force of 50N. The output of the load cell is a voltage, but a calibration curve can be used to translate the voltage into a force (in this case, the relationship is F=30.96*V). Using the robotics-control software, the center of the first opening and the center of the last opening are identified. The fabric hand screening is run using Symyx' Impressionist™ and Epoch™ software. The probe is translated to a position slightly above the sample centered on the opening, and moved the probe downwards at a relatively slow speed (~5–10 mm/sec), and collects the response of the load cell as force is applied to the sample. This is repeated for each sample on the array. When the program is finished with its data collection, a suitable fitting routine goes back and fits each peak in the voltage versus time output, identifying such values as peak height and peak width. These parameters are saved to a database, from where they can be later retrieved along with the actual load-displacement curves.

The screening process takes approximately 5 seconds per sample allowing the entire array of 24 samples to be screened in less than 2 minutes. The peak height of each of the load-displacement curves is used to rank the fabric hand of the 6 different binders. The ranking of fabric hand using the above-described rapid serial technique yielded results matching human panel fabric handle screens as shown in Table 1. The fabric materials are correlated from soft to stiff with increasing peak height. For comparison by a human panel test, panelists are asked to rank the fabric samples in the array from 1 to 6 for softest to stiffest. The total points a sample received is divided by the number of panelists to obtain the ranking. In the human panel test, half of the participants rank the array samples in the same order as the rapid serial test and the other half have two array samples switched.

TABLE 1

| Sample Identification | Peak height | Force applied to sample | Ranking by Human Panel |
|---|---|---|---|
| A | 0.0552 | 1.71 N | 1 |
| B | 0.0761 | 2.36 N | 2 |
| C | 0.0786 | 2.43 N | 3.5 |
| D | 0.1059 | 3.28 N | 3.5 |
| E | 0.2604 | 8.06 N | 5 |
| F | 0.2631 | 8.15 N | 6 |

Other Screens

The present invention may be employed by itself or in combination with other screening protocols for the analysis of liquids or their constituents. Without limitation, examples of such screening techniques include those addressed in commonly-owned U.S. Pat. No. 6,182,499 (McFarland et al); U.S. Pat. No. 6,175,409 B1 (Nielsen et al); U.S. Pat. No. 6,157,449 (Hajduk et al); U.S. Pat. No. 6,151,123 (Nielsen); U.S. Pat. No. 6,034,775 (McFarland et al); U.S. Pat. No. 5,959,297 (Weinberg et al), U.S. Pat. No. 5,776,359 (Schultz et al.), all of which are hereby expressly incorporated by reference herein.

Screening techniques may also include (without limitation) optical screening, infrared screening, electrochemical screening, flow characterization (e.g., gas, liquid or gel-phase chromatography), spectrometry, crystallography, or the like.

As one non-limiting example of the present invention, sample materials of gels that may be formed from Knox Gelatine. Accordingly, Knox Gelatine brand gelatin is dissolved in hot water at various concentrations, and equal volumes (300 ul each) are placed in the wells of a microtiter plate and refrigerated overnight. The samples are then sequentially probed with a 3/16" diameter stainless steel probe with a rounded end. The probe is placed above the gel surface of each of the sample materials and moved downward at a velocity of 5 mm/second while the force is recorded. The recorded force for each sample initially increases at a regular rate. Then the regular rate experiences a sudden decrease indicating failure of each of the material samples (i.e., gel strength failure). The measurement thus provides information on both elastic and failure properties of each of the sample materials. The force applied to each of the samples can be graphed or otherwise visually displayed versus time for data analysis purposes.

It should be understood that the invention is not limited to the exact embodiment or construction which has been illustrated and described but that various changes may be made without departing from the spirit and the scope of the invention.

What is claimed is:

1. A method for screening an array of materials for a frictional force, comprising:
    providing a library of at least four material samples;
    applying one or more translational or rotational forces to each of the at least four material samples with one or more probes wherein the one or more probes contact the material samples and are moved by an automatic system for applying the one or more forces;
    monitoring a response of each of the at least four material samples to the one or more forces; and
    correlating the response of each of the at least four material samples to a frictional force of each of the at least four material samples, the frictional force resisting the movement of the one or more probes.

2. A method as in claim 1, wherein the step of providing a library of at least four material samples includes placing each of the at least four material samples on a single substrate.

3. A method as in claim 2, further comprising lowering the temperature of the at least four material samples prior to applying the one or more forces to the at least four material samples.

4. A method as in claim 2, further comprising raising the temperature of the at least four material samples prior to applying the one or more forces to the at least four material samples.

5. A method as in claim 2, further comprising raising or lowering the humidity surrounding the at least four material samples.

6. A method as in claim 2, wherein a first of said one or more forces is applied to a first of the at least four material samples no more than five minutes previous to applying a second of said one or more forces to a second of the at least four material samples.

7. A method as in claim 1, wherein said library includes at least 16 different material samples.

8. A method as in claim 1, wherein the step of providing the material samples includes attaching one or more panel materials to a substrate.

9. A method as in claim 8, wherein the step of providing the material samples includes dispensing at least four aliquots of liquid upon discrete locations of the one or more panel material for forming the at least four material samples.

10. A method as in claim 9, wherein the at least four aliquots of liquid are at least slightly varied with respect to amount or composition.

11. A method as in claim 1, wherein the step of applying one or more forces to each of the at least four material samples with one or more probes includes contacting a surface of the one or more probes with a surface of the at least four material samples and urging the surface of the one or more probes to slide relative to the surface of the at least four material samples.

12. A method as in claim 1, wherein said library includes at least 16 different materials, each attached to a single substrate and wherein the throughput rate of testing the at least 16 different materials is no greater than 10 minutes per material.

13. A method as in claim 1, wherein said automatic system includes a robot arm.

14. A method for measuring a frictional force of a plurality of material samples, the method comprising the steps of:

providing a library comprising at least four different material samples; and serially measuring the frictional force of each of the at least four different material samples at a throughput rate no greater than about 5 minutes per material sample, wherein the frictional force is measured by contacting one or more probes to the at least four different materials samples with an automatic system for applying one or more translational or rotational forces.

15. A method as in claim 14, wherein the library includes at least 8 different material samples.

16. A method as in claim 14, wherein the library includes at least 16 different material samples.

17. A method of claim 14, wherein the frictional force of the at least four material samples is measured at an average sample-throughput of not more than about 2 minutes per material sample.

18. A method of claim 14 wherein the library comprises at least 8 material samples and at least about 50% of the at least 8 material samples are different from each other.

19. A method of claim 14, wherein the library comprises at least 16 material samples and at least 75% of the at least 16 material samples are different from each other.

20. A method for screening an array of materials for a frictional force, comprising:

providing one or more panel materials;

attaching the one or more panel material to a substrate;

dispensing at least four aliquots of liquid upon at least four discrete locations of the one or more panel materials for forming at least four panel material samples, each of the one or more panel materials providing an exposed surface;

contacting a surface of the one or more panel materials with a surface of one or more probes using an automated system;

urging the surface of the one or more probes to translate or rotate across the exposed surface of the at least four panel materials;

measuring the resistance of the surface of the one or more material samples to the urging of the one or more probes;

ranking the one or more material samples relative to each other based upon the measured resistance.

21. A method of claim 19, wherein the one or more panel materials are fabrics and the at least four aliquots of liquid are softeners.

* * * * *

UNITED STATES PATENT AND TRADEMARK OFFICE
Certificate

Patent No. 6,736,017 B2                                                                 Patented: May 18, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Mary Beth Kossuth, San Jose, CA; Damian A. Hajduk, San Jose, CA; Paul Mansky, San Francisco, CA; and Oleg Kolosov, San Jose, CA.

Signed and Sealed this Fifth Day of October 2004.

EDWARD LEFKOWITZ
*Supervisory Patent Examiner*
Art Unit 2855